(12) United States Patent
Marks et al.

(10) Patent No.: US 6,291,695 B1
(45) Date of Patent: *Sep. 18, 2001

(54) ORGANO-LEWIS ACIDS OF ENHANCED UTILITY, USES THEREOF, AND PRODUCTS BASED THEREON

(75) Inventors: Tobin J. Marks, Evanston, IL (US); You-Xian Chen, Midland, MI (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/329,765

(22) Filed: Jun. 10, 1999

Related U.S. Application Data

(60) Continuation-in-part of application No. 09/220,741, filed on Dec. 23, 1998, which is a division of application No. 08/800,548, filed on Feb. 18, 1997, now Pat. No. 5,856,256
(60) Provisional application No. 60/011,920, filed on Feb. 20, 1996.

(51) Int. Cl.[7] ..................................................... C07F 17/00
(52) U.S. Cl. ................. 556/53; 566/7; 502/152; 502/102; 502/103; 502/104; 502/117; 526/134; 526/170; 526/172; 526/943
(58) Field of Search ................. 526/134, 170, 526/172, 348, 943; 502/152, 102, 103, 104, 117; 556/7, 53

(56) References Cited

U.S. PATENT DOCUMENTS

| | | | |
|---|---|---|---|
| 3,950,435 | 4/1976 | Takahashi et al. | 260/613 R |
| 3,966,453 | 6/1976 | Takahashi et al. | 71/105 |
| 5,064,802 | 11/1991 | Stevens et al. | 502/102 |
| 5,296,433 | 3/1994 | Siedle et al. | 502/103 |
| 5,300,598 | 4/1994 | Marks et al. | 526/160 |
| 5,330,948 | 7/1994 | Marks et al. | 502/102 |

(List continued on next page.)

FOREIGN PATENT DOCUMENTS

| | | |
|---|---|---|
| 0416815 | 3/1991 | (EP) . |
| 0427697 | 5/1991 | (EP) . |
| 0468651 | 1/1992 | (EP) . |
| 0561479 | 9/1993 | (EP) . |
| 0573403 | 12/1993 | (EP) . |
| 9729845 | 8/1997 | (WO) . |
| 9735893 | 10/1997 | (WO) . |
| 9832776 | 7/1998 | (WO) . |
| 9841530 | 9/1998 | (WO) . |
| 9850392 | 11/1998 | (WO) . |

OTHER PUBLICATIONS

Beck et al., "Binuclear Zirconocene Cations with $\mu$–$Ch_3$–bridges in Homogeneous Ziegler–Natta Catalyst Systems", Journal of Molecular Catalysis A: Chemical 111, 1996, pp. 67–79.

(List continued on next page.)

Primary Examiner—David W. Wu
Assistant Examiner—Caixia Lu
(74) Attorney, Agent, or Firm—Sieberth & Patty, L.L.C.

(57) ABSTRACT

The organo-Lewis acids are novel triarylboranes which are highly fluorinated. Triarylboranes of one such type contain at least one ring substituent other than fluorine. These organoboranes have a Lewis acid strength essentially equal to or greater than that of the corresponding organoborane in which the substituent is replaced by fluorine, or have greater solubility in organic solvents. Another type of new organoboranes have 1–3 perfluorinated fused ring groups and 2-0 perfluorophenyl groups. When used as a cocatalyst in the formation of novel catalytic complexes with d- or f-block metal compounds having at least one leaving group such as a methyl group, these triorganoboranes, because of their ligand abstracting properties, produce corresponding anions which are capable of only weakly, if at all, coordinating to the metal center, and thus do not interfere in various polymerization processes such as are described.

27 Claims, 7 Drawing Sheets

U.S. PATENT DOCUMENTS

| | | | |
|---|---|---|---|
| 5,332,706 | 7/1994 | Nowlin et al. | 502/107 |
| 5,391,661 | 2/1995 | Naganuma et al. | 502/102 |
| 5,391,789 | 2/1995 | Rohrmann | 556/11 |
| 5,455,366 | 10/1995 | Rohrmann et al. | 556/8 |
| 5,468,708 | 11/1995 | Cooley et al. | 502/162 |
| 5,473,028 | 12/1995 | Nowlin et al. | 526/114 |
| 5,486,632 | 1/1996 | Devore et al. | 502/103 |
| 5,496,960 | 3/1996 | Piers et al. | 556/7 |
| 5,498,581 | 3/1996 | Welch et al. | 502/102 |
| 5,500,398 | 3/1996 | Marks et al. | 502/103 |
| 5,502,017 | 3/1996 | Marks et al. | 502/103 |
| 5,539,068 | 7/1996 | Devore et al. | 526/126 |
| 5,550,265 | 8/1996 | Castellanos et al. | 556/58 |
| 5,554,775 | 9/1996 | Krishnamurti et al. | 556/7 |
| 5,582,764 | 12/1996 | Nakashima et al. | 252/299.61 |
| 5,596,054 | 1/1997 | Takeuchi | 502/103 |
| 5,599,761 | 2/1997 | Turner | 502/152 |
| 5,602,067 | 2/1997 | Nowlin et al. | 502/104 |
| 5,721,183 | 2/1998 | Neithamer | 502/103 |
| 5,728,784 | 3/1998 | Po' et al. | 502/102 |
| 5,753,578 | 5/1998 | Santi et al. | 556/53 |
| 5,756,611 | 5/1998 | Etherton et al. | 526/127 |
| 5,786,495 | 7/1998 | Resconi et al. | 556/11 |
| 5,856,256 | 1/1999 | Marks et al. | 502/152 |

OTHER PUBLICATIONS

Bochmann et al., "Monomer–Dimer Equilibria in Homo– and Heterodinuclear Cationic Alkylzirconium Complexes and Their Role in Polymerization Catalysis", Angew Chem. Int. Ed. Engl., 1994, vol. 33, No. 15/16, pp. 1634–1637.

Chen et al., "Constrained Geometry" Dialkyl Catalysts. Efficient Syntheses, C–H Bond Activation Chemistry, Monomer–Dimer Equilibration, and α–Olefin Polymerization Catalysis, Organometallics, 1997, vol. 16, No. 16, pp. 3649–3657.

Chen et al., "Sterically Encumbered (Perfluoroaryl) Borane and Aluminate Cocatalysts for Tuning Cation–Anion Ion Pair Structure and Reactivity in Metallocene Polymerization Processes. A Synthetic, Structural, and Polymerization Study", J. Am. Chem. Soc., 1998, vol. 120, No. 25, pp. 6287–6305.

Chen et al., "Organo–Lewis Acids as Cocatalysts in Cationic Metallocene Polymerization Catalysis. Unusual Characteristics of Sterically Encumbered Tris(perfluorobiphenyl)borane", J. Am. Chem. Soc. 1996, vol. 118, No. 49, pp. 12451–12452.

Fenton et al., "Perfluorophenyl Derivatives of the Elements II. (Pentafluorophenyl)lithium, A Source of $_2$–Substituted Nonafluorobiphenyls", J. Organomental. Chem., vol. 2, 1964, pp. 437–446.

Jia et al., "Cationic Metallocene Polymerization Catalysts Based on Tetrakis(pentafluorophenyl)borate and Its Derivatives. Probing the Limits of Anion "Noncoordination" via a Synthetic, Solution Dynamic, Structural, and Catalytic Olefin Polymerization Study", Orgmet., 1997, vol. 16, No. 5, pp. 842–857.

Li et al., "New Organo–Lewis Acids. Tris(β–perfluoronaphthyl)borane (PNB) as a Highly Active Cocatalyst for Metallocene–Mediated Ziegler–Natta α–Olefin Polymerization", Organometallics, 1998, vol. 17, No. 18, pp. 3996–4003.

Piers et al., "Pentafluorophenylboranes: From Obscurity to Applications", Chemical Society Reviews, 1997, vol. 26, pp. 345–354.

Siedle et al., "How coordinating are Non–coodinating Anions?", Macromol Symp., 1995, vol. 89, pp. 299–305.

Yang et al., "Models for Organometallic Molecule–Support Complexes. Very Large Counterion Modulation of Cationic Actinide Alkyl Reactivity", Organometallics, 1991, vol. 10, pp. 840–842.

Marks, Tobin, J., "Surface–Bound Metal Hydrocarbyls. Organometallic Connections between Heterogeneous and Homogeneous Catalysts", Accounts of Chemical Research, 1992, vol. 25, No. 2, pp. 57–65.

Yang et al., "Cationic Zirconocene Olefin Polymerization Catalysts Based on the Organo–Lewis Acid Tris(pentafluorophenyl)borane. A Synthetic, Structural, Solution Dynamic, and Polymerization Catalytic Study", J. Am. Chem. Soc., 1994, No. 116, pp. 10015–10031.

Chemistry, With Inorganic Qualitative Analysis, Second Edition, Therald Moeller et al., Academic Press, 1984, p. 225.

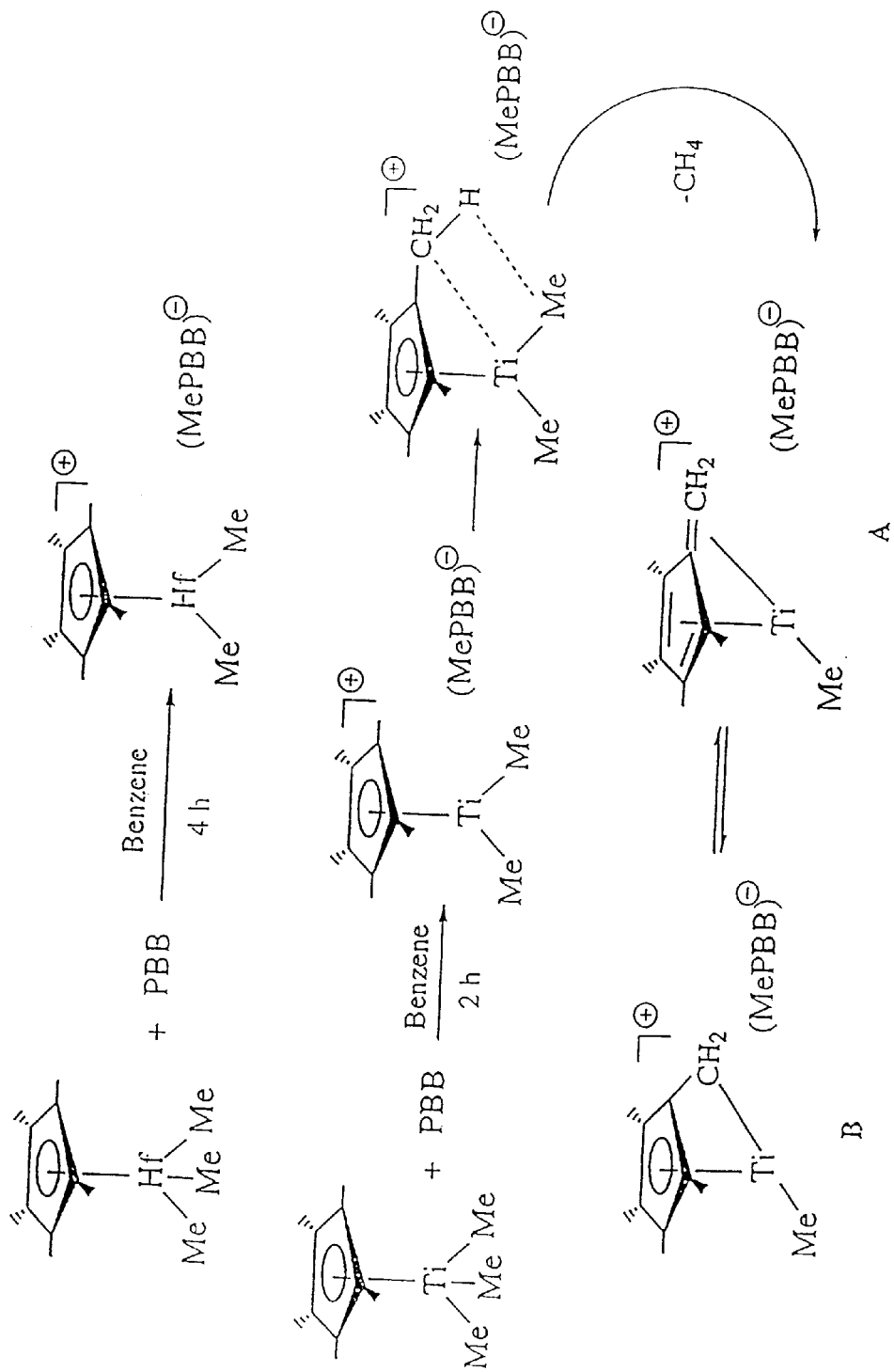

US 6,291,695 B1

ORGANO-LEWIS ACIDS OF ENHANCED UTILITY, USES THEREOF, AND PRODUCTS BASED THEREON

REFERENCE TO RELATED APPLICATIONS

This application is a continuation-in-part of prior copending application Ser. No. 09/220,741, filed Dec. 23, 1998, which is a division of application Ser. No. 08/800,548, filed Feb. 18, 1997, now U.S. Pat. No. 5,856,256, issued Jan. 5, 1999, which in turn claims the benefit of U.S. provisional application Ser. No. 60/011,920, filed Feb. 20, 1996. Reference is also made to commonly-owned U.S. application Ser. No. 09/329,431, filed Jun. 10, 1999.

This invention was made with Government support under Contract No. DE-FG02-86ER13511 awarded by the Department of Energy. The Government has certain rights in this invention.

BACKGROUND OF THE INVENTION

This invention relates, inter alia, to novel compositions of matter useful, inter alia, as cocatalysts, to novel catalyst compositions made using such cocatalysts, to methods for preparing these catalysts, and to methods for polymerization utilizing the catalysts.

The use of soluble Ziegler-Natta type catalysts in the polymerization of olefins is well known in the prior art. In general, such systems include a Group 4 metal compound and a metal or metalloid alkyl cocatalyst, such as aluminum alkyl cocatalyst. More broadly, it may be said to include a mixture of a Group 1, 2 or 13 metal alkyl and a transition metal complex from Group 4–5 metals, particularly titanium, zirconium, or hafnium with aluminum alkyl cocatalysts.

First generation cocatalyst systems for homogeneous metallocene Ziegler-Natta olefin polymerization, alkylaluminum chlorides (AlR$_2$Cl), exhibit low ethylene polymerization activity levels and no propylene polymerization activity. Second generation cocatalyst systems, utilizing methyl aluminoxane (MAO), raise activities by several orders of magnitude. In practice however, a large stoichiometric excess of MAO over catalyst ranging from several hundred to ten thousand must be employed to have good activities and stereoselectivities. Moreover, it has not been possible to isolate characterizable metallocene active species using MAO. The third generation of cocatalyst, B(C$_6$F$_5$)$_3$, proves to be far more efficient while utilizing a 1:1 catalyst-cocatalyst ratio. Although active catalyst species generated with B(C$_6$F$_5$)$_3$ are isolable and characterizable, the anion MeB(C$_6$F$_5$)$_3^\ominus$, formed after Me$^\ominus$ abstraction from metallocene dimethyl complexes, is weakly coordinated to the electron-deficient metal center, thus resulting in a drop of certain catalytic activities. The recently developed B(C$_6$F$_5$)$_4^\ominus$ type of non-coordinating anion exhibits some of the highest reported catalytic activities, but such catalysts have proven difficult to obtain in the pure state due to poor thermal stability and poor crystallizability, which is crucial for long-lived catalysts and for understanding the role of true catalytic species in the catalysis for the future catalyst design. Synthetically, it also takes two more steps to prepare such an anion than for the neutral organo-Lewis acid.

In our prior applications referred to hereinabove, and in publications appearing in *J. Am. Chem. Soc.* 1996, 118, 12451–12452, *Organometallics* 1998, 17, 3996–4003, and *J. Am. Chem. Soc.* 1998, 120, 6287–6305 new, sterically encumbered fluoroaryl boranes such as tris(perfluorobiphenyl)borane (PBB), and the preparation and use of such compounds as a catalyst for ring opening polymerization of tetrahydrofuran (THF) and as a highly efficient cocatalyst for metallocene-mediated olefin polymerization are described. For example, PBB is a strong organo-Lewis acid which can be synthesized in much higher yield than B(C$_6$F$_5$)$_3$. The anion generated with PBB is non-coordinating instead of being weakly coordinating as in the case of B(C$_6$F5)$_3$. Thus, the former exhibits higher catalytic activities and can activate previously unresponsive metallocenes. The catalytically active species generated with PBB are isolable, X-ray crystallographically characterizable instead of the unstable, oily residues often resulting in the case of B(C$_6$F$_5$)$_4^\ominus$. In addition, PBB exhibits even higher catalytic activities in most cases.

This invention provides, inter alia, technology described in the above-referred-to prior applications, and additionally, improvements in the technology described in the above-referred-to prior applications.

SUMMARY OF THE INVENTION

Accordingly, it is an object of the subject invention to provide, prepare and utilize new types of organo-Lewis acids that are useful in forming novel, highly-effective olefin polymerization catalysts.

A further object of the subject invention is to provide a catalyst which permits better control over molecular weight, molecular distribution, stereoselectivity, and/or comonomer incorporation.

Another object of the subject invention is to provide a Ziegler-Natta type catalyst system which reduces the use of excess cocatalyst and activates previously unresponsive metallocenes.

In accordance with one of its embodiments this invention provides novel organoboranes which may be represented by the formula

wherein R' is a fluoroaryl group having at least one additional substituent other than fluorine, wherein each R" is, independently, (i) a fluoroaryl group having at least one additional substituent other than fluorine, or (ii) a fluorinated aryl group devoid of additional substitution, and wherein n is 1 or 2. In these compounds both R" groups are preferably the same as each other and, preferably, are fluoroaryl groups having at least one additional substituent other than fluorine. Most preferably, n is 3, and each R' of formula (I) is the same as the other two. The substituent(s) other than fluorine present in the organoboranes of formula (I) can be (i) one or more substituents which increase the solubility of the compound in an organic solvent as compared to the corresponding compound in which each such substituent other than fluorine is replaced by a fluorine atom, (ii) one or more electron withdrawing substituents other than fluorine, or (iii) a combination of at least one substituent from (i) and at least one substituent from (ii).

A second embodiment provides organoboranes which may be referred to by the formula

where at least one of R' and R" is a fluorinated biphenyl or fluorinated polycyclic fused ring group such as naphthyl, anthracenyl or fluorenyl. Preferably two, and more preferably all three, of R' and R" are fluorinated biphenyl or fluorinated polycyclic fused ring groups such as naphthyl, anthracenyl or fluorenyl. Two of the biphenyl groups may be substituted with a phenyl group. That is, R' is a biphenyl group and each R" is a phenyl group. The biphenyl groups and the phenyl groups plus any polycyclic fused ring group or groups of the compounds of formula (II) should be highly fluorinated, preferably with only one or two hydrogen atoms on a group, and most preferably, as in PBB, with no hydrogen atoms and all fluorine substituents. Thus in one subgroup of these triorganoboranes R' of formula (II) is a fluorobiphenyl group having 0 to 2 hydrogen atoms and 7 to 9 fluorine atoms on the rings thereof, the sum of the foregoing integers being 9, and each R" of formula (II) is a phenyl group having 0 to 2 hydrogen atoms and 3 to 5 fluorine atoms on the ring, the sum of the foregoing integers being 5. In this subgroup most preferably R' is nonafluorobiphenyl and each R" group is a pentafluorophenyl group, i.e., the compound is nonafluorobiphenyl-bis(pentafluorophenyl)borane. In another subgroup of these triorganoboranes R' of formula (II) is a fluorobiphenyl group having 0 to 2 hydrogen atoms and 7 to 9 fluorine atoms on the rings thereof, the sum of the foregoing integers being 9, and each R" group of formula (II) is a fluorinated polycyclic fused ring group such as naphthyl, anthracenyl or fluorenyl. Preferably the polycyclic fused ring group is perfluorinated. However the fused rings may have one or two hydrogen atoms on the ring with the other available positions occupied by fluorine. A third subgroup of organoboranes of this second embodiment are tris(fluorobi-phenyl)boranes wherein R' of formula (II) and each R" of formula (II) is a fluorobiphenyl group having 0 to 2 hydrogen atoms and 7 to 9 fluorine atoms on the rings thereof, the sum of the foregoing integers being 9, especially where such fluorobiphenyl groups are all the same as each other. The most preferred compound of this third sub-group is tris(perfluorobi-phenyl)borane.

A third embodiment of this invention is comprised of organoboranes of the formula:

$$B(R^1)_n(R^2)_{3-n} \quad (III)$$

wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3. Such compounds include, for example:

tris(nonafluoroanthracenyl)borane,
bis(nonafluoroanthracenyl)(pentafluorophenyl)borane,
nonafluoroanthracenylbis(pentafluorophenyl)borane,
tris(undecafluorotetrahydronaphthyl)borane,
bis(undecafluorotetrahydronaphthyl)(pentafluorophenyl)borane,
undecafluorotetrahydronaphthylbis(pentafluorophenyl)borane,
tris(nonafluorofluorenyl)borane,
bis(nonafluorofluorenyl)(pentafluorophenyl)borane, and
nonafluorofluorenylbis(pentafluorophenyl)borane.

Compounds of this embodiment in which less than half of the fluorine atoms, and preferably up to about 3 fluorine atoms, are replaced by a corresponding number of substituents other than fluorine are included within the scope of the first embodiment described above.

A fourth embodiment of this invention provides a novel complex or ion pair formed from an organoborane of the first embodiment. In particular, the novel complex or ion pair of this fourth embodiment comprises a cation formed from a d-block or f-block metal compound by abstraction therefrom of a leaving group (e.g., a methyl group), and an anion formed by unification of the leaving group with an organoborane of the formula $BR'_nR''_{3-n}$. In this formula, R' is a fluoroaryl group having at least one additional substituent other than fluorine, wherein each R' is, independently, (i) a fluoroaryl group having at least one additional substituent other than fluorine, or (ii) a fluorinated hydrocarbyl group devoid of additional substitution, and n is 1 or 2.

A fifth embodiment of this invention provides a novel complex or ion pair formed from an organoborane of the third embodiment. Thus in accordance with this fifth embodiment the complex or ion pair comprises a cation formed from a d-block or f-block metal compound by abstraction therefrom of a leaving group (e.g., a methyl group), and an anion formed by unification of the leaving group with an organoborane of the formula $B(R^1)_n(R^2)_{3-n}$. In this formula, each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3.

In a sixth embodiment of this invention, a novel catalytic complex or ion pair is produced by a process which comprises contacting a d-block or f-block metal compound having at least one leaving group (e.g., a methyl group) with an organoborane of the formula $BR'_nR''_{3-n}$. In this formula, R' is a fluoroaryl group having at least one additional substituent other than fluorine, each R" is, independently, (i) a fluoroaryl group having at least one additional substituent other than fluorine, or (ii) a fluorinated hydrocarbyl group devoid of additional substitution, and n is 1 or 2. In this process, which typically is conducted in a suitable anhydrous liquid solvent and in a suitably inert atmosphere or environment, a leaving group is abstracted from the d-block or f-block metal compound and becomes unified with the organoborane to produce the catalytic complex.

A seventh embodiment is analogous to the process of the sixth embodiment except that the organoborane has the formula $B(R^1)_n(R^2)_{3-n}$ wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3.

An eighth embodiment of this invention is a process for polymerizing an olefinic monomer or copolymerizing two or more olefinic monomers, which process comprises contacting the monomer or monomers, preferably a single vinyl monomer or two or more copolymerizable vinyl monomers, with a polymerization catalyst complex which comprises a cation formed from a d-block or f-block metal compound by abstraction therefrom of a leaving group (e.g., a methyl group), and an anion formed by unification of the leaving group with an organoborane of the formula $BR'_nR''_{3-n}$ wherein R' is a fluoroaryl group having at least one additional substituent other than fluorine, wherein each R" is, independently, (i) a fluoroaryl group having at least one additional substituent other than fluorine, or (ii) a fluorinated hydrocarbyl group devoid of additional substitution, and wherein n is 1 or 2.

A ninth embodiment is analogous to the polymerization process of the eighth embodiment except that the organoborane has the formula $B(R^1)_n(R^2)_{3-n}$ wherein each $R^1$ is, independently, a perfluorinated polycyclic fused ring group in which the ring system is totally aromatic (e.g., as in naphthyl or anthracenyl), or is partially aromatic and partially cycloaliphatic, (e.g., as in tetrahydronaphthyl, acenaphthyl, indenyl, or fluorenyl), wherein each $R^2$ is a pentafluorophenyl group, and wherein n is 1 to 3.

These and other objects, embodiments, features and advantages of this invention will be apparent from the ensuing description, appended claims, and accompanying Drawings.

BRIEF DESCRIPTION OF THE DRAWINGS

FIG. 4 shows the reaction pathway for another type of catalytic complex formed from PBB;

FIG. 5 shows the reaction pathway for still another type of catalytic complex formed from PBB;

Figure 1:
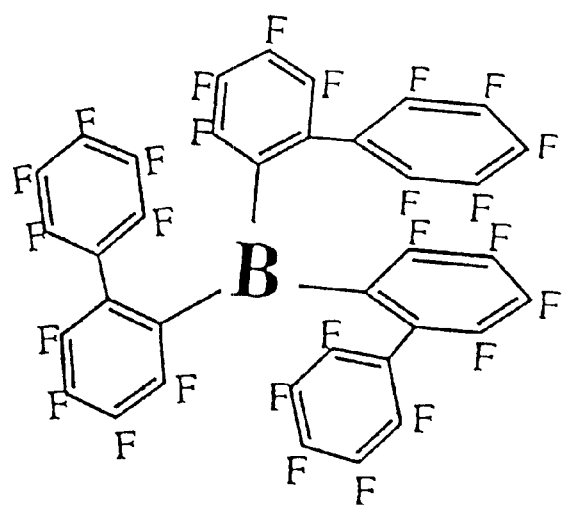
FIG. 1 is a structural depiction of PBB.

Pathways analogous to those depicted in FIGS. 3–9 exist when PBB is replaced by (a) an analogous triorganoborane of formula (I) above in which n is 3 and in which the three R' groups are all the same as each other, (b) a triorganoborane of formula (II) above in which the R' group and the two R" groups are all the same as each other, and (c) a triorganoborane of formula (III) above in which n is 3, and all three $R^1$ groups ire the same as each other.

It is to be understood that the present invention is not to be limited to any spatial configurations for complexes depicted either in the Figures or in the specification or claims of this document. Such depictions are not presented as limitations or requirements as regards stereochemical considerations, but rather are presented for purposes of illustration only.

FURTHER DETAILED DESCRIPTION OF THE INVENTION

Organoboranes of this Invention

The compounds of the first, second, and third embodiments of this invention are strong organo-Lewis acids. When used as a cocatalyst in the formation of our novel catalyst compositions, these triorganoboranes, because of their ligand abstracting properties, produce corresponding anions which are capable of only weakly, if at all, coordinating to the metal center, and thus do not interfere in the olefin polymerization processes.

As noted above, the novel, eminently useful organoboranes of the first embodiment of this invention can be represented by formula (I), i.e., $BR'_n R''_{3-n}$. In this formula R' is a fluoroaryl group having at least one additional substituent other than fluorine (hereinafter sometimes called a "substituted fluoroaryl group"), R" is, independently, (i) a substituted fluoroaryl group, or (ii) a fluorinated aryl group devoid of additional substitution (hereinafter sometimes called an "unsubstituted fluoroaryl group"), and n is 1 or 2. It will, of course, be understood that the term "substituent" in reference to the ring system of the fluoroaryl group does not include a hydrogen or deuterium atom—the substituent is something other than these. Each fluoroaryl group is highly fluorinated. Thus preferably, each substituted fluoroaryl group has (a) more fluorine atoms than such other ring substituents, (b) no more than three such other ring substituents, and at most only one hydrogen atom on the ring. More preferably, each substituted fluoroaryl group has (a) no more than two such other substituents on the ring, (b) no hydrogen atom on the ring, and (c) a fluorine atom in each of the other ring positions available for substitution. Similarly, each unsubstituted fluoroaryl group preferably contains no more than two hydrogen atoms on the ring, and more preferably no more than one hydrogen atom on the ring. Most preferably, an unsubstituted fluoroaryl group is perfluorinated.

The substituents other than fluorine on the ring(s) of R' can be, for example, one or more of the following:

hydrocarbyloxy, RO—;
hydrocarbylthio, RS—;
tri(hydrocarbyl)silyl, $R_3Si$—;
dihydrocarbylamino, $R_2N$—;
dihydrocarbylphosphino, $R_2P$—;
hydrocarbyl, R—;
trihydrocarbylsiloxy, $R_3SiO$—;
dihydrocarbyloxidoamino, $R_2N(O)$—;
dihydrocarbyloxidophosphino, $R_2P(O)$—;
poly(hydrocarbyloxy), $R(OR')_nO$—, where R' is divalent hydrocarbyl, e.g., methylene (—$CH_2$—), dimethylene (—$CH_2CH_2$—), methyldimethylene (—$CH(CH_3)CH_2$—), ethyldimethylene (—$CH(C_2H_5)CH_2$—), cyclohexylene (—$C_6H_{10}$—), phenylene (—$C_6H_4$—), or the like, and n is 1 to about 100, and preferably 1 to about 50;
poly(hydrocarbylsiloxy), $R_3SiO(R_2SiO)_nR_2SiO$—, where n is 0 to about 20); and
halide of atomic number greater than 9.

In the above formulas of the substituent groups, R, independently, is cyclic or acyclic or a group having both cyclic and acyclic portions, is saturated or contains aliphatic or aromatic unsaturation or both, and typically has no more than about 24 carbon atoms, and preferably no more than about 12 carbon atoms. In addition, the hydrocarbyl moiety of the above substituents can itself be substituted, e.g., by one or more groups such as halide, hydroxy, alkoxy, or analogous substituents. Thus the substituents other than fluorine atoms on the ring(s) of the fluoroaryl groups can be, for example, substituted hydrocarbyloxy, substituted hydrocarbylthio, substituted trihydrocarbylsilyl where 1 to 3 of the hydrocarbyls are substituted, substituted dihydrocarbylamino where one or both hydrocarbyls are substituted, substituted dihydrocarbylphosphino where one or both hydrocarbyls are substituted, substituted hydrocarbyl other than fluoroaryl, or substituted trihydrocarbylsiloxy where 1 to 3 of the hydrocarbyls are substituted.

Preferably, the organoborane of formula (I) is (i) a Lewis acid of a strength essentially equivalent to or, more preferably, greater than that of the corresponding organoborane in which each substituent other than fluorine is replaced by a fluorine atom or (ii) a Lewis acid having greater solubility in organic solvents. For the purposes of this invention, comparative Lewis acid strength is assessed by reacting bis(cyclopentadienyl)-thorium dimethyl with the respective organoboranes and the extent of ion pair formation is determined by NMR. Similarly, comparative solubility in organic solvents is measured by determining the solubility of the respective organoboranes in n-hexane at 20° C.

Illustrative examples of some of the preferred organoboranes of this invention are presented in the following formulas wherein x is 1 to 3, and R is a substituent other than a fluorine atom, typically an electron-withdrawing group or a solubility-enhancing group. In formulas (IV) through (X), one or more of the fluorine atoms, typically no more than three fluorine atoms on any given fused ring structure depicted, may be replaced by such a substituent.

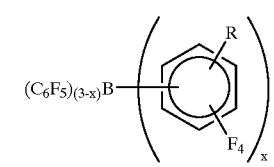

Formula (IV)

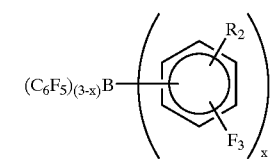

Formula (V)

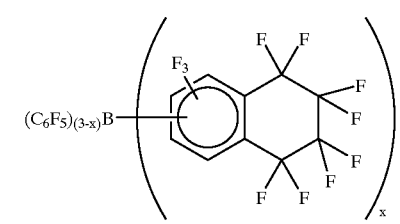

Formula (VI)

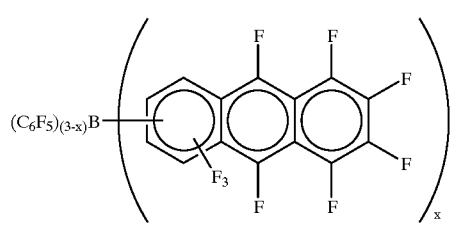

Formula (VII)

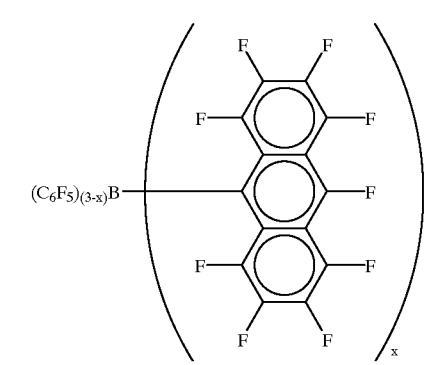

Formula (VIII)

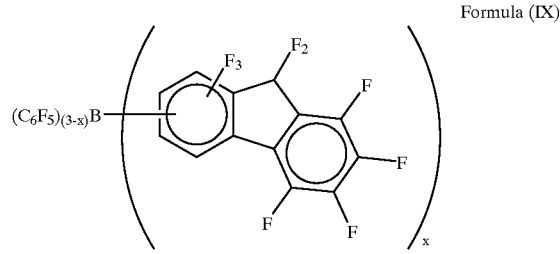

Formula (IX)

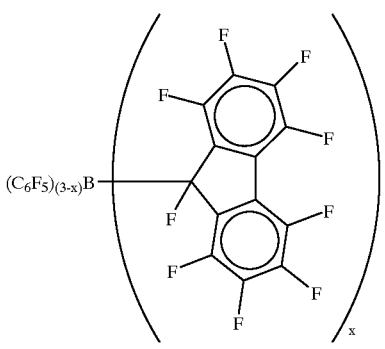

Formula (X)

The organoboranes of this invention can be prepared by reaction between (i) an active metal derivative of the polyfluoroaromatic or substituted polyfluoroaromatic compound corresponding in structure to the structure(s) desired for R', and if present, R", or $R^1$, and if present, $R^2$, and (ii) a boron trihalide or an etherate complex thereof. Thus in preparing a triorganoborane of formula (I) above in which R' and R" are all the same substituted fluoroaryl groups, the reaction may be depicted by the following equation:

$$3M-R'+BX_3 \rightarrow B(R')_3+3MX \qquad (Eq. 1)$$

where M is an alkali metal (e.g., Li or Na), Al, Sn, Zn, Hg, or a halomagnesium group, R' is a fluoroaryl group having at least one ring substituent other than fluorine, and X is a halogen atom. When preparing a triorganoborane of formula (I) above wherein one or each of two of the fluoroaryl groups is a substituted fluoroaryl group and each of the two remaining fluoroaryl groups or the one remaining fluoroaryl group differs therefrom (e.g., it is an unsubstituted fluoroaryl group, or it is a different substituted fluoroaryl group), the reaction depicted in Equation (2) can be used:

$$n\ Mb\ R'+B(R")_{3-n}X_n \rightarrow B(R')_{n(R")3-n}+n\ MX \qquad (Eq. 2)$$

where M, R', and X are as defined above in connection with equation (1), R" is a fluoroaryl group that is different from R', and n is 1 or 2. An analogous two-step procedure is employed when the three fluoraryl groups are to differ from each other.

Reactions pursuant to Equations (1) and (2) above can also be used for preparing triorganoboranes of formula (II) above by using reactants in which R', and if present, R" are as defined in connection with formula (II). For example, PBB (FIG. 1) has been synthesized via Equation (1) in yields as high as 91% as compared to the 30–50% yields experienced with $B(C_6F_5)_3$, currently a very important Lewis acidic cocatalyst in industry. The Lewis acidity of PBB has been shown to be much greater than that of $B(C_6F5)_3$ by comparative reactions of $Cp^*_2ThMe_2$ with $B(C_6F_5)_3$ and PBB ($Cp^*=C_5Me_5$). The former reagent does not effect $Me^\ominus$ abstraction, while the latter gives methyl abstraction in forming, for example, the catalyst shown in FIG. 3. Preferred compounds of formula (I), (II), or (III) above having a Lewis acid strength essentially equivalent to, and preferably greater than, that of PBB also possess this important property.

Similarly, reactions pursuant to Equations (1) and (2) above can be used for preparing triorganoboranes of formula (III) above. In this case R' in these equations is replaced by $R^1$, and R" is replaced by $R^2$, where $R^1$ and $R^2$ are as defined above in connection with formula (III).

Figure 2:
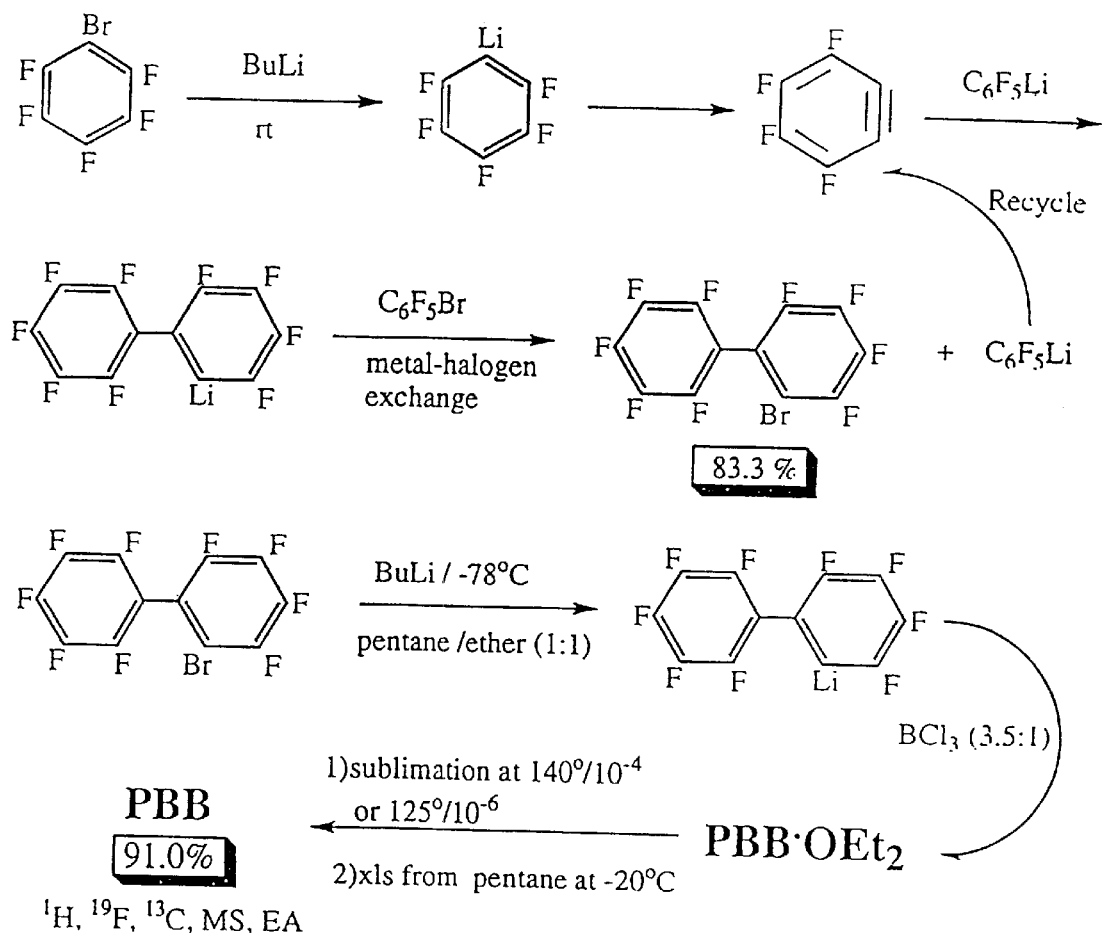
FIG. 2 is a reaction pathway for the synthesis of PBB, which pathway is equally applicable to the synthesis of (a) analogous triorganoboranes of formula (I) above in which n is 3 and in which the three R' groups are all the same as each other, (b) triorganoboranes of formula (II) above in which the R' group and the two R" groups are all the same as each other, and (c) triorganoboranes of formula (III) above in which n is 3, and all three $R^1$ groups are the same as each other.
Figure 3:
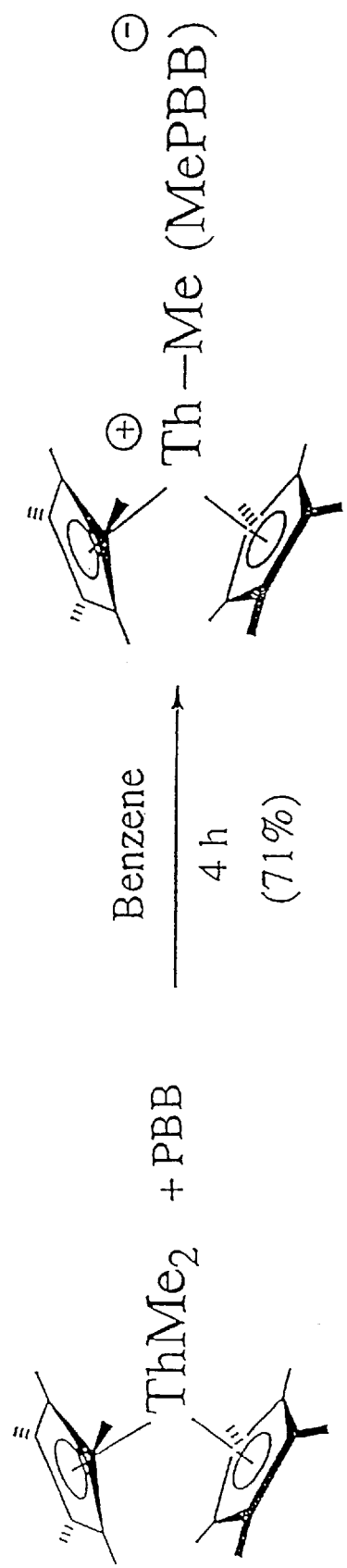
FIG. 3 shows the reaction pathway for one type of catalytic complex formed from PBB.

The reactions of Equations (1) and (2) are typically conducted in a suitable non-coordinating solvent such as a liquid paraffinic or aromatic hydrocarbon or mixture thereof, and typically at temperatures in the range of about $-78°$ C. to about $25°$ C. However, ether [) solvents can be used, either alone or in combination with a hydrocarbon solvent. When an ether solvent is employed, the product will typically be coordinated with the ether, which is then removed, for example by sublimation. FIG. 2 and Example 1 hereinafter illustrate an overall synthesis for PBB, involving, inter alia, Equation (1) above. As noted, such synthesis can readily be adapted for synthesis of organoboranes of formulas (I), (II), and (III) above in which all three fluoroaryl groups are the same. Likewise, Example 2 hereinafter illustrates a synthesis procedure of Equation (2) above that can be used for producing triorganoboranes having two different fluoroaryl groups in the molecule. By appropriate substitution of reactants in this procedure, a variety of such triorganoboranes of this invention can be prepared.

Catalytic Complexes of this Invention

The reaction of tris(2-perfluorobiphenyl)borane and of bis(perfluorophenyl)(2-perfluorobiphenyl)borane with a variety of zirconocene and other actinide or transition metal dimethyl complexes proceeds rapidly and quantitatively at room temperature in noncoordinating solvents to yield catalytic complexes. These catalytic complexes may be used in the polymerization, copolymerization, oligomerization and dimerization of α-olefins. In addition, each of these catalytic complexes may be used together with aluminum alkyls, aluminum aryls, (e.g., $AlR_3$, R=Me, Et, Ph, naphthyl) or alumoxanes (which are also known as aluminoxanes), such as methylalumoxane for increased polymer yields. This invention now makes it possible, inter alia, to synthesize a wide variety of other new catalytic complexes which can be used in the same manner for producing homopolymers, copolymers, oligomers and dimers of α-olefins. These new catalytic complexes can also be used in conjunction with hydrocarbyl aluminum compounds or alumoxanes in the efficient polymerization of various monomers of suitable, if not enhanced, properties.

Pursuant to this invention a d- or f- block metal compound having at least one leaving group is reacted with a triorganoborane of this invention whereby a leaving group is abstracted from the metal compound to produce a cation, and the abstracted leaving group is unified with the triorganoborane to form an anion.

Various d- and f- block metal compounds may be used in forming the catalytically active compounds of this invention. The d-block and f-block metals of this reactant are the transition, lanthanide and actinide metals. See, for example, the Periodic Table appearing on page 225 of Moeller, et al., *Chemistry*, Second Edition, Academic Press, Copyright 1984. References herein to Groups of the Periodic Table are made with reference to the Periodic Table appearing on page 225 of Moeller et al. As regards the metal constituent, preferred are compounds of Groups 4–8 of the Periodic Table. More preferred are compounds of the metals of Groups 4–6 (Ti, Zr, Hf, V, Nb, Ta, Cr, Mo, and W) and thorium, and most preferred are thorium and the Group 4 metals, titanium and hafnium, and especially zirconium.

A vital feature of the d- or f-block metal compound used in forming the catalytic complexes of this invention is that it must contain at least one leaving group that is abstracted by and unifies with the triorganoborane of this invention whereby an ion pair is formed. Univalent leaving groups that meet these criteria include hydride, hydrocarbyl free of hydrogen atoms in a β-position, and silylcarbinyl ($R_3SiCH_2$—) groups. Examples include methyl, benzyl, and trimethylsilylcarbinyl. Of these, the methyl group is the most preferred leaving group.

Metallocenes make up a preferred class of d- and f-block metal compounds used in making the catalytic complexes of this invention. These compounds are characterized by containing at least one cyclopentadienyl moiety pi-bonded to the metal atom. For use in this invention, the metallocene must also have bonded to the d- or f-block metal atom at least one leaving group capable of being abstracted by and unified with the triorganoborane used.

Metallocene structures in this specification are to be interpreted broadly, and include structures containing 1, 2, 3 or 4 Cp or substituted Cp rings. Thus metallocenes suitable for use in this invention can be represented by the formula XI:

$$Q_a Cp_b M L_c X_d \quad\quad\quad (XI)$$

where Cp independently in each occurrence is a cyclopentadienyl-moiety-containing group which typically has in the range of 5 to about 24 carbon atoms; Q is a bridging group or ansa group that links two Cp groups together; M is a d- or f-block metal atom; each L is, independently, a leaving group that is bonded to the d-or f-block metal atom and is capable of being abstracted by the triorganoborane used in forming the catalytic complex; X is a group other than a leaving group that is bonded to the d- or f-block metal atom; a is 0 or 1; b is a whole integer from 1 to 3 (preferably 1 or 2); c is 1 to 3; d is 0 or 1; and the sum of c and d is at least 2. The sum of b, c, and d is sufficient to form a stable compound, and often is the formal oxidation state (or formal valence) of the d- or f-block metal atom. When using as a polymerization catalyst a complex of this invention made from a metallocene of formula (XI), X, if present, must not detrimentally affect propagation of the polymer chain during polymerization. In such case, X is preferably a hydrogen atom or a group bonded to the metal atom via a carbon atom, and most preferably, is a hydrogen atom or an alkyl group.

Cp is, independently, a cyclopentadienyl, indenyl, 4,5,6,7-tetrahydroindenyl, 1-azaindenyl, fluorenyl, or related group, including a benzo-fused indenyl and an acenaphthindenyl group as described in U.S. Pat. No. 5,455,366, or a hydrocarbyl-, halo-, halohydrocarbyl-, hydrocarbylmetalloid-, and/or halohydrocarbylmetalloid-substituted derivative of any of the foregoing groups, as long as the group can π-bond to the metal. Cp typically contains up to 75 non-hydrogen atoms. Q, if present, is typically a silylene (>$SiR_2$), benzo ($C_6H_4$<), substituted benzo, methylene (—$CH_2$—), substituted methylene, ethylene (—$CH_2CH_2$—), or substituted ethylene bridge. M is preferably a metal atom of Groups 4–8, and most preferably is thorium or a Group 4 metal atom, especially titanium, and most especially zirconium. L is the leaving group, such as hydride, or benzyl, and which in most cases is methyl. X, if present, is a non-leaving group, and thus can be a halogen atom, a non-leaving hydrocarbyl group, hydrocarbyloxy, (alkoxy, aryloxy, etc.), trihydrocarbyl-siloxy, and similar univalent groups that form stable metallocenes. The sum of b, c, and d is a whole number, and is often from 3–5. When M is a Group 4 metal or an actinide metal, and b is 2, the sum of c and d is 2, c being at least 1. When M is a Group 3 or lanthanide metal, and b is 2, c is 1 and d is zero. When M is a Group 5 metal, and b is 2, the sum of c and d is 3, c being at least 2.

In one preferred group of metallocene reactants of formula (XI), b is 2, i.e., there are two cyclopentadienyl-moiety containing groups in the molecule, and these two groups can be the same or they can be different from each other.

In another preferred group of metallocene reactants, b in formula (XI) is 1, i.e., there is only one cyclopentadienyl-moiety containing group in the molecule, and typically the sum of c and d is 3.

Also suitable for preparing catalytic complexes of this invention are compounds analogous to those of formula (XI) where one or more of the Cp groups are replaced by cyclic unsaturated charged groups isoelectronic with Cp, such as borabenzene or substituted borabenzene, azaborole or substituted azaborole, and various other isoelectronic Cp analogs. See for example Krishnamurti, et al., U.S. Pat. Nos. 5,554,775 and 5,756,611.

Another sub-group of useful metallocenes which can be used in the practice of this invention are metallocenes of the type described in WO 98/32776 published Jul. 30, 1998. These metallocenes are characterized in that one or more cyclopentadienyl groups in the metallocene are substituted by one or more polyatomic groups attached via a N, O, S, or P atom or by a carbon-to-carbon double bond. Examples of such substituents on the cyclopen-tadienyl ring include —OR, —SR, —NR$_2$, —CH═, —CR═, and —PR$_2$, where R can be the same or different and is a substituted or unsubstituted C$_1$–C$_{16}$ hydrocarbyl group, a tri-C$_1$–C$_8$ hydrocarbylsilyl group, a tri-C$_1$–C$_8$ hydrocarbyloxysilyl group, a mixed C$_1$–C$_8$ hydrocarbyl and C$_1$–C$_8$ hydrocarbyloxysilyl group, a tri-C$_1$–C$_8$ hydrocarbylgermyl group, a tri-C$_1$–C$_8$ hydrocarbyloxygermyl group, or a mixed C$_1$–C$_8$ hydrocarbyl and C$_1$–C$_8$ hydrocarbyloxygermyl group.

Still another subgroup of preferred metallocenes is comprised of the so-called constrained geometry metal complexes. See for example U.S. Pat. No. 5,539,068 and references cited therein at Column 1, lines 44–57. The constrained geometry complexes suitable for use in preparing catalytic complexes of this invention can be represented by the formula:

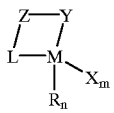

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group, n is 1 to 4, m is 0 to 3, with the sum of n plus m being 1 to 4 depending upon the valence of M. Of such compounds, preferred are those in which M is titanium or zirconium, L is a cyclopentadienyl group or a substituted cyclopentadienyl group, Z is a dihydrocarbylsilyl group, Y is a hydrocarbylamido group, R is methyl, n is 2, and m is 0. Particularly preferred compounds of this type are those in which M is titanium or zirconium, L is a tetramethylcyclopentadienyl group, Z is a dimethylsilyl group, Y is a tert-butylamido group, R is methyl, n is 2, and m is 0. The same comments regarding X as made in connection with formula (XI) above, also apply to the group designated X in the above formula. Thus, as noted above, most preferably X is a hydrogen atom or an alkyl group.

Illustrative examples of suitable d- or f-block metal compounds that can be used as reactants in forming the catalytic complexes of this invention can be found, for example, in U.S. Pat. Nos. 5,391,789; 5,498,581; 5,786,495; and in WO 98/50392 A1, published Nov. 12, 1998, provided of course that the compound contains, or is modified to contain, at least one leaving group.

Examples of metallocenes to which this invention is applicable include such compounds as:
bis(methylcyclopentadienyl)titanium dimethyl;
bis(methylcyclopentadienyl)zirconium dimethyl;
bis(n-butylcyclopentadienyl)zirconium dimethyl;
bis(dimethylcyclopentadienyl)zirconium dimethyl;
bis(diethylcyclopentadienyl)zirconium dimethyl;
bis(methyl-n-butylcyclopentadienyl)zirconium dimethyl;
bis(n-propylcyclopentadienyl)zirconium dimethyl;
bis(2-propylcyclopentadienyl)zirconium dimethyl;
bis(methylethylcyclopentadienyl)zirconium dimethyl;
bis(indenyl)zirconium dimethyl;
bis(methylindenyl)zirconium dimethyl;
dimethylsilylenebis(indenyl)zirconium dimethyl;
dimethylsilylenebis(2-methylindenyl)zirconium dimethyl;
imethylsilylenebis(2-ethylindenyl)zirconium dimethyl;
dimethylsilylenebis(2-methyl-4-phenylindenyl)zirconium dimethyl;
1,2-ethylenebis(indenyl)zirconium dimethyl;
1,2-ethylenebis(methylindenyl)zirconium dimethyl;
2,2-propylidenebis(cyclopentadienyl)(fluorenyl)zirconium dimethyl;
dimethylsilylenebis(6-phenylindenyl)zirconium dimethyl;
bis(methylindenyl)zirconium benzyl methyl;
ethylenebis[2-(tert-butyldimethylsiloxy)-1-indenyl] zirconium dimethyl;
dimethylsilylenebis(indenyl)chlorozirconium methyl;
5-(cyclopentadienyl)-5-(9-fluorenyl)1-hexene zirconium dimethyl;
dimethylsilylenebis(2-methylindenyl)hafnium dimethyl;
dimethylsilylenebis(2-ethylindenyl)hafnium dimethyl;
dimethylsilylenebis(2-methyl-4-phenylindenyl)hafnium dimethyl;
2,2-propylidenebis(cyclopentadienyl)(fluorenyl)hafnium dimethyl;
bis(9-fluorenyl)(methyl)(vinyl)silane zirconium dimethyl,
bis(9-fluorenyl)(methyl)(prop-2-enyl)silane zirconium dimethyl,
bis(9-fluorenyl)(methyl)(but-3-enyl)silane zirconium dimethyl,
bis(9-fluorenyl)(methyl)(hex-5-enyl)silane zirconium dimethyl,
bis(9-fluorenyl)(methyl)(oct-7-enyl)silane zirconium dimethyl,
(cyclopentadienyl)(1-allylindenyl)zirconium dimethyl,
bis( 1-allylindenyl)zirconium dimethyl,
(9-(prop-2-enyl)fluorenyl)(cyclopentadienyl)zirconium dimethyl, (9-(prop-2-enyl)fluorenyl)(pentamethylcyclopentadienyl) zirconium dimethyl,
bis(9-(prop-2-enyl)fluorenyl)zirconium dimethyl,
(9-(cyclopent-2-enyl)fluorenyl)(cyclopentadienyl) zirconium dimethyl,
bis(9-(cyclopent-2-enyl)(fluorenyl)zirconium dimethyl,
5-(2-methylcyclopentadienyl)-5-(9-fluorenyl)-1-hexene zirconium dimethyl,
1-(9-fluorenyl)-1-(cyclopentadienyl)-1-(but-3-enyl)-1-(methyl)methane zirconium dimethyl,
5-(fluorenyl)-5-(cyclopentadienyl)-1-hexene hafnium dimethyl,
(9-fluorenyl)(1-allylindenyl)dimethylsilane zirconium dimethyl,
1-(2,7-di(α-methylvinyl)(9-fluorenyl)-1-(cyclopentadienyl)-1,1-dimethylmethane zirconium dimethyl,
1-(2,7-di(cyclohex-1-enyl)(9-fluorenyl))-1-(cyclopentadienyl)-1,1-methane zirconium dimethyl,
5-(cyclopentadienyl)-5-(9-fluorenyl)-1-hexene titanium dimethyl,
5-(cyclopentadienyl)-5-(9-fluorenyl)1-hexene titanium dimethyl,
bis(9-fluorenyl)(methyl)(vinyl)silane titanium dimethyl,
bis(9-fluorenyl)(methyl)(prop-2-enyl)silane titanium dimethyl,
bis(9-fluorenyl)(methyl)(but-3-enyl)silane titanium dimethyl,
bis(9-fluorenyl)(methyl)(hex-5-enyl)silane titanium dimethyl,
bis(9-fluorenyl)(methyl)(oct-7-enyl)silane titanium dimethyl,
(cyclopentadienyl)(1-allylindenyl)titanium dimethyl,
bis(1-allylindenyl)titanium dimethyl,
(9-(prop-2-enyl)fluorenyl)(cyclopentadienyl)hafnium dimethyl,
(9-(prop-2-enyl)fluorenyl)(pentamethylcyclopentadienyl) hafnium dimethyl,
bis(9-(prop-2-enyl)fluorenyl)hafnium dimethyl,
(9-(cyclopent-2-enyl)fluorenyl)(cyclopentadienyl)hafnium dimethyl,
bis(9-(cyclopent-2-enyl)(fluorenyl)hafnium dimethyl,
5-(2-methylcyclopentadienyl)-5-(9-fluorenyl)-1-hexene hafnium dimethyl,
5-(fluorenyl)-5-(cyclopentadienyl)-1-octene hafnium dimethyl,
(9-fluorenyl)(1-allylindenyl)dimethylsilane hafnium dimethyl.
(tert-butylamido)dimethyl(tetramethylcyclopentadienyl) silane titanium dimethyl;
(cyclopentadienyl)(9-fluorenyl)diphenylmethane zirconium dimethyl;
(cyclopentadienyl)(9-fluorenyl)diphenylmethane hafnium dimethyl;
dimethylsilanylene-bis(indenyl)thorium dimethyl;
dimethylsilanylene-bis(4,7-dimethyl-1-indenyl)zirconium dimethyl;
dimethylsilanylene-bis(indenyl)uranium dimethyl;
dimethylsilanylene-bis(2-methyl-4-ethyl-1-indenyl) zirconium dimethyl;
dimethylsilanylene-bis(2-methyl-4,5,6,7-tetrahydro-1-indenyl)zirconium dimethyl;
(tert-butylamido)dimethyl(tetramethyl-$\eta^5$-cyclopentadienyl)silane titanium dimethyl;
(tert-butylamido)dimethyl(tetramethyl-$\eta^5$-cyclopentadienyl)silane chromium dimethyl;
(tert-butylamido)dimethyl(tetramethyl-$\eta^5$-cyclopentadienyl)silane titanium dimethyl; and
(phenylphosphido)dimethyl(tetramethyl-$\eta^5$-cyclopentadienyl)silane titanium dimethyl.

In many cases the metallocenes such as referred to above will exist as racemic mixtures, but pure enantiomeric forms or mixtures enriched in a given enantiomeric form can be used.

A few illustrative examples of catalytically active catalytic complexes of this invention include the following, wherein G is a moiety corresponding to an organoborane of any of formulas (IV) to (X), above.

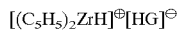

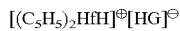

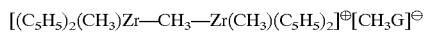

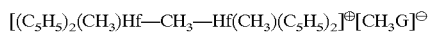

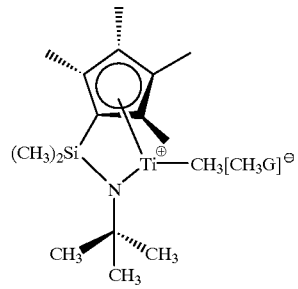

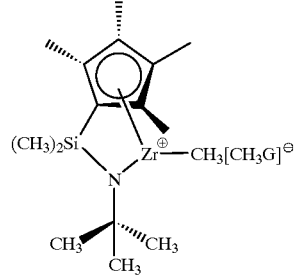

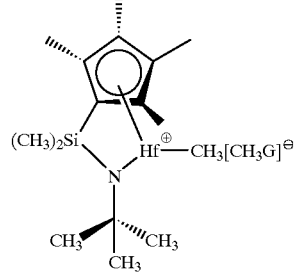

-continued

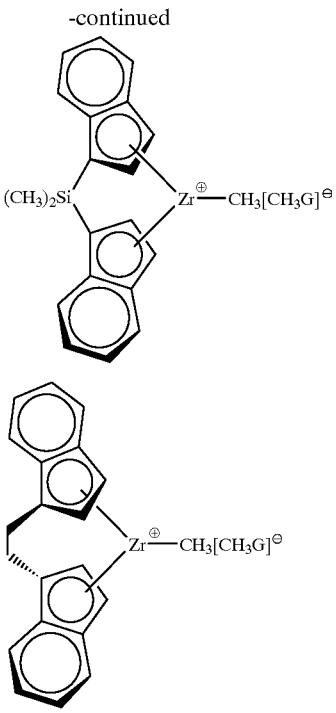

The equations presented below illustrate some of the reactions used in forming the new catalytic complexes of this invention. In these equations Cp represents a cyclopentadienyl moiety-containing group. Other abbreviations used in various portions of this document include the following:
Cp'=$\eta^5$-$C_5H_5$
Cp*=$\eta^5$-$Me_5C_5$
Cp"=$\eta^5$-1,2-$Me_2C_5H_3$
CGC=($\eta^5$-$Me_4C_5$)$SiMe_2N^tBu$
Ind=$\eta^5$-$C_9H_7$ (Indenyl)
Flu=$\eta^5$-$C_{13}H_9$ (Fluorenyl)

It is also worth noting that in accordance with common practice in the art, the designations "$\mu$-Me", "$\mu$-H", and "$\mu$-F" signify that the indicated group or element constitutes a bridge between two metal centers.

Reaction of a compound of formula (I) above with a bis-Cp type of dimethyl metallocene such as a zirconocene can form a dinuclear methyl-bridged metallocene cation, for example:

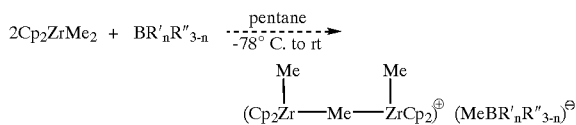

When this reaction is performed in the presence of hydrogen, a dinuclear hydrogen bridged metallocene cation can be formed, for example:

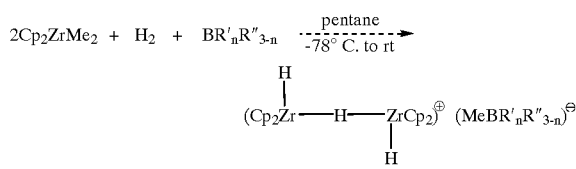

More particularly, reaction of an organoborane of formula (I) above with a Group 4 dimethyl or trimethyl or a Th dimethyl at temperatures in the range of about −78° C. to about 25° C. proceeds cleanly to yield cationic complexes such as set forth below.

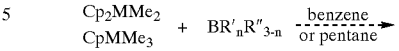

M=Th, Zr, Hf, Ti
1. $[Cp*_2ThMe^\oplus[MeBR'_nR"_{3-n}]^\ominus$
2. $[Cp'_2ZrCl]^\oplus[MeBR'_nR"_{3-n}]^\ominus$
3. $[Cp'_2ZrMe(\mu-Me)MeZrCp_2]^\oplus[MeBR'_nR"_{3-n}]^\ominus$
4. $[Cp"_2ZrMe(\mu-Me)MeZrCp"_2]^\oplus[MeBR'_nR"_{3-n}]^\ominus$
5. $[Cp*_2ZrMe(\mu-Me)MeZrCp*_2]^\oplus[MeBR'_nR"_{3-n}]^\ominus$
6. $\{[(Me_4C_5)SiMe_2N^tBu]ZrMe\}^\oplus[MeBR'_nR"_{3-n}]^\ominus$
7. $\{[(Me_4C_5)SiMe_2N^tBu]TiMe\}^\oplus[MeBR'_nR"_{3-n}]^\ominus$
8. $[Cp*ZrMe_2]^\oplus[MeBR'_nR"_{3-n}]^\ominus$
9. $[Cp*HfMe_2]^\oplus[MeBR'_nR"_{3-n}]^\ominus$
10. $\{[rac-Me_2Si(Ind)_2ZrMe]_2(\mu-Me)\}^\oplus[MeBR'_nR"_{3-n}]^\ominus$
11. $\{[Me_2C(Flu)(Cp)ZrMe]_2(\mu-Me)\}^\oplus[MeBR'_nR"_{3-n}]^\ominus$ Monomeric metallocene cations such as zirconocene cations can be produced by reacting an organoborane of formula (I) with a bis-Cp type of dimethyl metallocene at a suitably elevated temperature. An example is the following reaction which may be performed at about 60° C.:

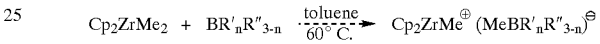

The same end product can be formed by another new reaction of this invention in which the methyl-bridged dinuclear metallocene is used as the starting material:

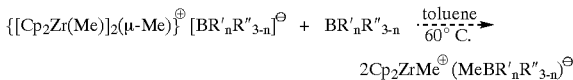

Another novel reaction of this invention results from the discovery that certain methyl-bridged dinuclear metallocenes can be thermally transformed to fluorine-bridged dinuclear metallocenes:

Other types of cationic metallocene catalyst systems can also be created with the organoboranes of this invention such as depicted in formulas (I), (II), and (III) above. For example, metallocene cations of mono-Cp type such as depicted in FIGS. 4 and 5 can be formed by the reaction of mono-pentamethyl Cp trimethyl Group 4 complexes with PBB. When PBB is replaced in these reactions by an organoborane of formula (I) the product contains an anion formed by the unification of a methyl leaving group with the organoborane. These are very good syndiospecific styrene polymerization catalysts.

Figure 6:
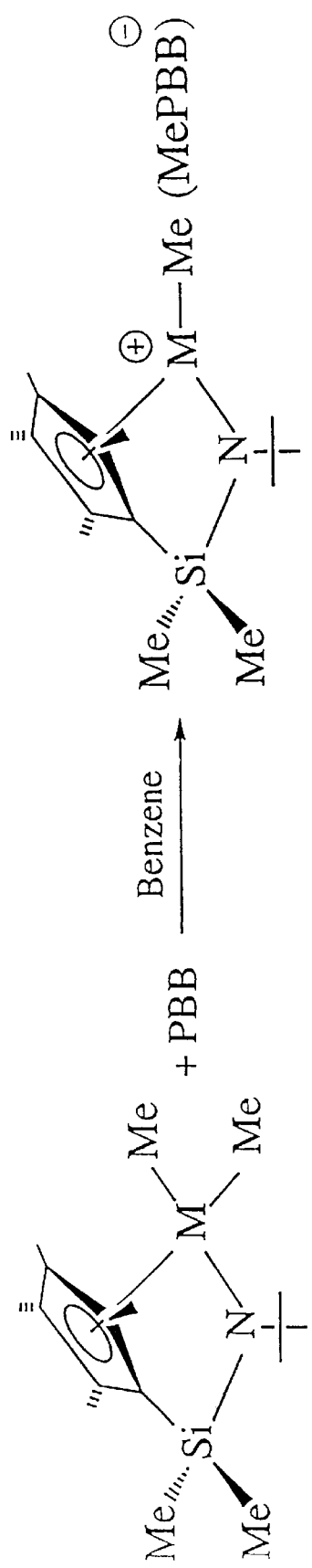
FIG. 6 shows the reaction pathway for yet another type of catalytic complex formed from PBB.
Figure 7:
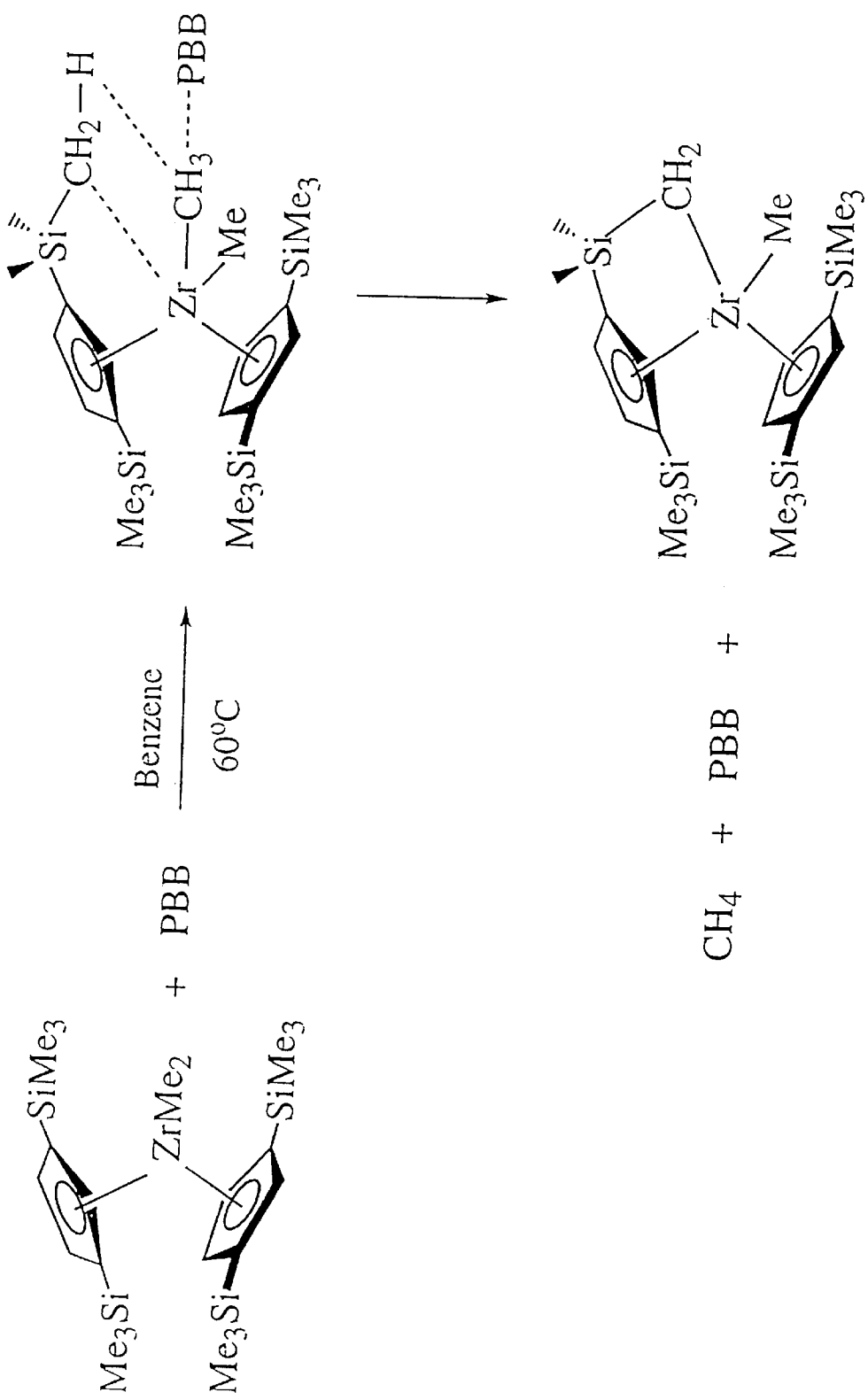
FIG. 7 shows the reaction pathway for another type of complex formed from PBB.
Figure 8:
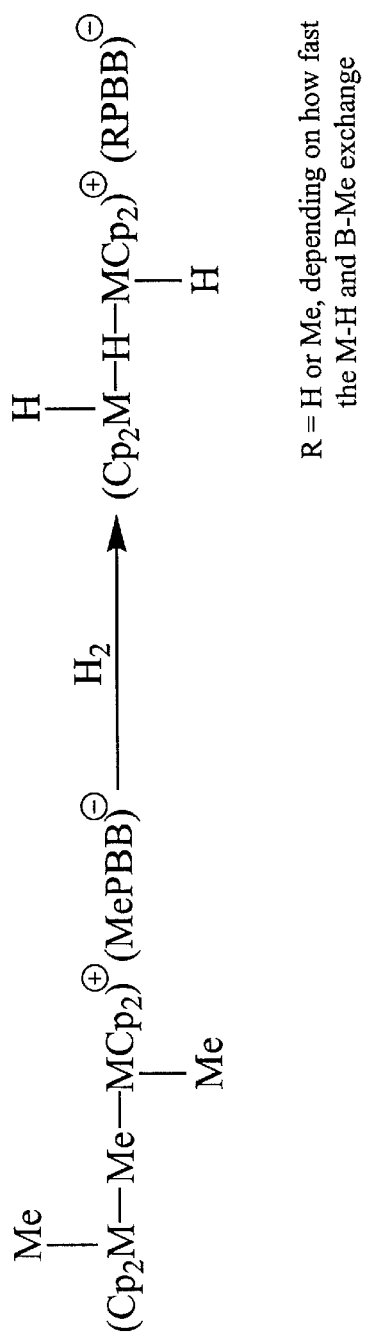
FIG. 8 shows a reaction pathway for a binuclear catalytic complex formed from PBB.
Figure 9:
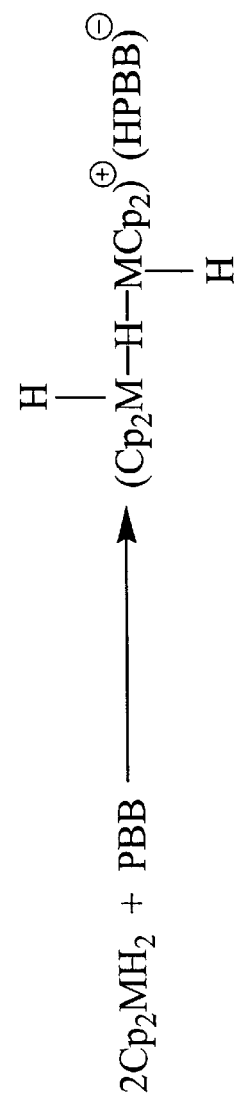
FIG. 9 shows another reaction pathway for a binuclear catalytic complex formed from PBB.

Constrained geometry types of zirconocene and titanocene cations such as those in FIG. 6 where M=Zr or Ti, are readily produced by the reaction of the corresponding dimethyl metallocenes with organoboranes of formulas (I), (II), and (III). The resultant catalytic complexes are highly naked cations, and are, in general, more active catalysts than those generated with $B(C_6F_5)_3$.

The following Examples are presented for purposes of illustration. They are not intended to limit, and should not be construed as limiting, the scope of this invention to the particulars set forth therein.

EXAMPLE 1

Synthesis of Tris(2-perfluorobiphenyl)borane (PBB)
a) n-Butyllithium (1.6 M in hexanes, 25 mL, 40 mmol) was added dropwise to bromopentafluorobenzene 18.0 g, 9.1 mL, 72.9 mmol) in 100 mL of diethyl ether over a cold-water bath. The mixture was then stirred for a further 12 h at room temperature. Removal of solvent followed by vacuum sublimation at 60–65° C./$10^{-4}$ torr gave 12.0 g of 2-bromononafluorobiphenyl as a white crystalline solid: yield 83.3%. The dangerous and explosive nature of $C_6F_5Li$ either solutions in this preparation can be avoided by (a) the use of excess of $C_6F_5Br$, (b) slow addition of n-butyllithium, (c) frequent change of the cold water bath or use of a continuous flowing cold water bath.

b) To the above prepared 2-bromononafluorobiphenyl (5.0 g, 12.7 mmol) in a mixed solvent of 70 mL of diethyl ether and 70 mL of pentane was gradually added 8.0 mL of n-butyllithium (1.6 M in hexanes, 12.8 mmol) at −78° C. The mixture was stirred for an additional 2 h, and boron trichloride (4.0 mL, 1.0 M in hexanes, 4.0 mmol) was then quickly added by a syringe. The mixture was left at −78° C. for 1 h and the temperature was then allowed to slowly rise to room temperature. A suspension resulted after stirring an additional 12 h. It was filtered to give a yellow solution, and the solvent of the filtrate was removed in vacuo. The resulting pale yellow powder was sublimed at 140° C./$10^{-4}$ torr or 125° C./$10^{-6}$ torr to produce a light yellow crystalline solid as an ether-free crude product. Recrystallization from pentane at −20° C. gave 3.5 g of the pure PBB as a white crystalline solid: yield 91.0%. Analytical and spectroscopic data for PBB are as follows. $^{19}F$ NMR ($C_6D_6$, 23° C.): δ−120.08 (s, br, 3 F, F-3), −132.09 (s, br, 3F, F-6), −137.66 (s, br, 6 F, F-2'/F-6'), −143.31 (t, $^3J_{F-F}$=21.4 Hz, 3 F, F-4), −149.19 (t, $^3JF-F$=21.7 Hz, 3 F. F-4'), −150.56 (t, $^3J_{F-F}$=14.7 Hz, 3 F, F-5), 160.72 (s, br, 6 F, F-3'/F-5'). $^{13}C$ NMR ($C_6D_6$, 23° C.): δ150.92 (dd, $^1J_{=C-F}$=251.8 Hz, $^2J_{C-F}$=10.1 Hz, 3 C), 146.35 (dd, $^1J_{C-F}$=254.3 Hz, $^2J_{C-F}$=12.1 Hz, 3 C), 144.26 (dd, $^1J_{C-F}$=258.1 Hz, $^2J_{C-F}$=10.5 Hz, 6 C). 143.50 (tt, $^1J_{C-F}$=265.4 Hz, $^2J_{C-F}$=12.0 Hz, 3 C), 141.98 (tt, $^1J_{C-F}$=261.4 Hz,=11.7 Hz, 3 C), 141.17 (tt, $^1J_{C-F}$=254.3 Hz, $^2J_{C-F}$=10.5 Hz, 3 C), 137.70 (tt. $^1J_{C-F}$=257.3 Hz. $^2J_{C-F}$=11.6 Hz, 6 C), 124.51 (d, $^2J_{C-F}$=11.7 Hz, 3 C), 113.60 (d, $^2J_{C-F}$=11.5 Hz. 3 C), 106.05 (s, br, 3 C). MS: parent ion at m/e 956. Anal. Calcd for $C_{36}BF_{27}$: C, 45.22: H, 0.00. Found: C, 45.44; H, 0.05.

EXAMPLE 2

Synthesis of Bis(pentafluorophenyl)(2-perfluorobiphenyl)borane (BPB)

In a 100 mL flask, 2-perfluorobiphenyl bromide (3.16 g, 8.0 mmol) was dissolved in 20 mL of dry pentane. To another 250 mL flask, were added 30 mL of pentane and 5.1 mL of n-butyllithium (1.6 M in hexanes, 9.0 mmol), and the solution was cooled down to −50° C. The solution of 2-perfluorobiphenyl bromide was added dropwise via syringe to the n-butyllithium solution. A white precipitate formed immediately. The resultant mixture was stirred between −40° C. and −30° C. for 90 minutes after the addition was completed, and then 20 mL of $(C_6F_5)_2BCl$ (3.16 g, 8.0 mmol in pentane) was added at −50° C. The reaction mixture was allowed to warm slowly to room temperature overnight. After filtration and removal of all the volatiles, a sticky oil was left. This oil was washed with cold pentane (−78° C.) three times to give a white solid product. Yield, 2.0 g (37%). The complex can be further purified by sublimation at 110° C. (0.05 torr) for 3 h. Spectroscopic and analytical data for (BPB) are as follows. $^{19}F$ NMR (benzene-$d_6$, 282.33 MHz, 23° C.) δ−127.48 (d, $^3J_{F-F}$=21.5 Hz, 4 F, o-F), −128.28 (m, 1 F, 3-F), −135.10 (m, 1 F, 6-F), −139.89 (d, $^3J_{F-F}$=21.5 Hz, 2 F, 2', 6'-F), −140.90 (tt, $^3J_{F-F}$=20.8 Hz, 2 F, p-F), −144.94 (td, $^3J_{F-F}$=21.0 Hz, $^5J_{F-F}$=7.6 Hz, 1 F, 5-F), −150.07 (t, $^3J_{F-F}$=21.2 Hz, 1 F, 4'-F), −151.48 (td, $^3J_{F-F}$=22.2 Hz, $^5J_{F-F}$=6.8 Hz, 1 F, 4-F), −160.25 (m, 4 F, m-F), −160.98 (m, 2 F, 3', 5'-F). Anal. Calcd for $C_{24}BF_{19}$: C, 43.67; H, 0.00; N, 0.00. Found C, 43.65, H, 0.10, N, 0.00.

EXAMPLE 3

Synthesis of $[Cp_2MMe]^{⊕}$ $[MePBB]^{⊖}$(M'Th; Cp=$C_5Me_5$)

$(C_5Me_5)_2ThMe_2$ (0.106 g, 0.199 mmol) and PBB (0.191 g, 0.199 mmol), in a glove box, were charged into a 25-mL reaction flask with a filter plug, and the flask was attached to a high vacuum line. Benzene (15 mL) was then vacuum-transferred into this flask at −78° C. The mixture was slowly allowed to warm to room temperature and stirred for 6 h. The solvent was removed, pentane (20 mL) was next vacuum-transferred into the flask, and the mixture was filtered after stirring. The white solid which collected was dried under vacuum to give 0.210 g of product: yield 70.9%. Analytical and spectroscopic data are as follows. $^1H$ NMR ($C_6D_6$, 23° C.): δ1.61 (s, 30 H, $C_{0.5}Me_5$), 0.62 (s, 3 H, Th—$CH_3$), −095 (s, br, 3 H, B—$CH_3$). $^{19}F$ NMR ($C_6D_6$, 23° C.): δ−124.57 (s, br, 3F), −138.10 (s, br, 3 F), −139.28 (d, $^3J_{F-F}$=21.4 Hz, 3 F), −139.74 (d, $^3J_{F-F}$=21.2 Hz, 3 F), −155.08 (t, $^3J_{F-F}$21.4 Hz, 3 F), −157.32 (t, $^3J_{F-F}$=22.0 Hz, 3 F), −162.20 (t, $^3J_{F-F}$=22.0 Hz, 3 F), −163.13 (t, $^3J_{F-F}$=22.0 Hz, 3 F), −163.90 (t, $^3J_{F-F}$=21.4 Hz, 3 F). $^{13}C$ NMR ($C_6D_6$, 23° C.): δ129.54 ($C_5Me_5$), 79.28 (Th—Me), 10.44 ($C_5Me_5$), 10.25 (B—Me). Anal. Calcd for $C_{58}H_{36}BF_{27}$ Th: C, 46.79; H, 2.44; N, 0.00. Found: C, 46.68; H, 2.24; N. 0.00.

EXAMPLE 4

Synthesis of $[Cp_2MCl]^{⊕}$DMePBB$]^{⊖}$(M=Zr; Cp=$C_5H_5$)

The procedure of Example 3 above was repeated using $(C_5H_5)_2Zr(Cl)Me$ instead of $(C_5Me_5)_2ThMe_2$. This resulted in production of $[(C_5H_5)_2ZrCl]^{⊕}[MePBB]^{⊖}$in 80% yield. Analytical and spectroscopic data for $[(C_5H_5)_2ZrCl]^{⊕}$ [MePBB]$^{⊖}$are as follows. $^1H$ NMR ($C_7D_8$, 23° C.): δ5.95 (s, 10 H, Cp), −0.94 (s, br, 3 H, B—$CH_3$). $^{19}F$ NMR ($C_6D_6$, 23° C.): δ−123.41 (s, br, 3 F), −139.24 (d, $^3J_{F-F}$=24.0 Hz, 3 F), −139.58 (d, $^3J_{F-F}$=21.4 Hz, 3 F), −139.87 (d, $^3J_{F-F}$=23.1 Hz, 3 F), −155.88 (t, $^3J_{F-F}$=21.4 Hz, 3 F), −159.22 (t, $^3J_{F-F}$=22.6 Hz, 3 F), −162.96 (t, $^3J_{F-F}$=21.7 Hz, 3 F), −163.63 (t, $^3J_{F-F}$=22.6 Hz, 3 F), −164.12 (t, $^3J_{F-F}$=25.4 Hz, 3 F).

EXAMPLE 5

Synthesis of $[Cp_2M(Me)(\mu\text{-}Me)(Me)MCp_2]^{⊕}$ $[MePBB]^{⊖}$(M=Zr; Cp=$C_5H_5$, $C_5H_3Me_2$, or $C_5Me_5$)

$Cp_2ZrMe_2$ (0.398 mmol) and PBB (0.199 mmol) were loaded into a 25 mL-flask, which was then attached to the vacuum line. Pentane (20 mL) was then vacuum-transferred into this flask at −78° C. The mixture was slowly warmed to room temperature and stirred for an additional 2 h (Cp=$C_5H_5$), 15 h (Cp=$C_5H_3Me_2$) or 48 h (Cp=$C_5Me_5$). The resulting suspension was filtered, and the colored solids (light pink for $C_5H_5$, light yellow for $C_5H_3Me_2$ and yellow for $C_5Me_5$) were washed with a small amount of pentane and dried under vacuum: yields 90.3% ($C_5H_5$), 86.3% ($C_5H_3Me_2$) and 34.7% ($C_5Me_5$). Analytical and spectroscopic data for the $C_5H_5$ complex are as follows. $^1H$ NMR ($C_6D_6$, 23° C.): δ5.65 (s, 20 H, $C_5H_5$), −0.04 (s, 6 H, Zr—CH$_3$), −0.84 (s, br, 3 H, B—CH$_3$), −1.15 (s, 3 H, Zr—CH$_3$—Zr). $^{19}$F NMR (C$_6$D$_6$, 23° C.): δ124.20 (d, $^3J_{F-F}$=16.6 Hz, 3 F), −138.98 (d, $^3J_{F-F}$=20.3 Hz, 3 F), −139.20 (d, $^3J_{F-F}$=22.0 Hz, 3 F), −140.29 (d, $^3J_{F-F}$=24.5 Hz, 3 F), −155.15 (t, $^3J_{F-F}$=20.9 Hz, 3 F), −160.06 (t, $^3J_{F-F}$=22.3 Hz, 3 F), −162.79 (t, $^3J_{F-F}$=22.0 Hz, 3 F), −163.11 (t, $^3J_{F-F}$=21.5 Hz, 3 F), −163.97 (t, $^3J_{F-F}$=19.0 H, 3 F). $^{13}$C NMR (C$_6$D$_6$, 23° C.): δ113.24 (C$_5$H$_5$), 38.88 (Zr—CH$_3$), 21.53 (B—CH$_3$), 15.80 (Zr—CH$_3$—Zr). Anal. Calcd for C$_{60}$H$_{32}$BF$_{27}$Zr$_2$: C, 49.39; H, 2.21; N, 0.00. Found: C, 48.97; H, 1.92; N 0.00.

Analytical and spectroscopic data for the C$_5$H$_3$Me$_2$ complex are as follows. $^1$H NMR (C$_7$D$_8$, 23° C.): δ5.51 (t, $^3J_{HH}$=2.8 Hz, 4 H, C$_5$H$_3$ Me$_2$), 5.47 '(t, $^3J_{H-H}$=3.2 Hz, 4 H C$_5$H$_3$Me$_2$), 5.18 (t, $^3J_{H-H}$=2.8 Hz, 4 H, C$_5$H$_3$Me$_2$). 1.73 (s, 12 H, C$_5$H$_3$Me$_2$), 1.51 (s, 12 H C$_5$H$_3$MMe$_2$), −0.26 (s, 6 H, Zr—CH$_3$), −0.92 (s, br, 3 H, B—CH$_3$), −1.50 (s,3 H, Zr—CH$_3$—Zr). $^{19}$F NMR (C$_6$D$_6$, 23° C.): δ123.37 (d, $^3J_{F-F}$=15.3 Hz, 3 F), −139.20 (d, $^3J_{F-F}$=24.0 Hz, 3 F −139.62 (d, $^3J_{F-F}$=24.3 Hz, 3 F), −139.89 (d, $^3J_{F-F}$=24.0 Hz, 3 F), −155.81 (t, $^3J_{F-F}$=2.14 Hz, 3 F), −159.36 (t, $^3J_{F-F}$=22.3 Hz, 3 F), −163.22 (t, $^3J_{F-F}$=21.4 Hz, 3 F), −16.55 (t, $^3J_{F-F}$=22.0 Hz, 3 F), −164.20 (t, $^3J_{F-F}$=22.6 Hz, 3 F). $^{13}$C NMR (C$_6$D$_6$, 23° C.): δ114.20 (d, $^1J_{CH}$=17.1 Hz, C$_5$H$_3$Me$_2$), 113.62 (s, C$_5$H$_3$Me$_2$), 112.80 (s, C$_5$H$_3$Me$_2$), 111.29 (d, $^1J_{CH}$=165.7 Hz, C$_5$H$_3$Me$_2$), 106,57 (d, $^1J_{CH}$=173.3 Hz. C$_5$H$_3$Me$_2$), 41.63 (q, $^1J_{C-H}$=118.4 Hz, Zr—CH$_3$), 31.26 (q, $^1J_{CH}$=116.5 Hz, B—CH$_3$), 22.21 (q, $^1J_{CH=134.3}$ Hz, Zr—CH$_3$—Zr, 12.94 (q, $^1J_{CH}$=128.0 Hz, C$_5$H$_2$Me$_2$), 12.71 (q, $^1J_{CH}$=127.6 Hz. C$_5$H$_2$Me$_2$). Anal. Calcd for C$_{68}$H$_{48}$BF$_{27}$Z$_2$: C, 51,98; H, 3.08; N, 0.00. Found: C, 51.61; H, 3.00; N, 0.00.

Analytical and spectroscopic data for the C$_5$Me$_5$ complex are as follows. $^1$H NMR (C$_6$D$_6$, 23° C.): δ1.57 (s, 60 H, C$_5$Me$_5$) −0.84 (s, br, 3 H, B—CH$_3$). The bridging and terminal methyl groups are discrete at low temperature. $^1$H NMR (C$_7$D$_8$, −13° C.): δ−0.19 (s, br, 6 H. Zr—CH$_3$), −0.92 (s, br, 3 H, B—CH$_3$), −2.42 (s, br, 3 H, Zr—CH$_3$—Zr). $^{19}$F NMR (C$_6$D$_6$, 23° C.): δ−123.11 (d, s, br, 3 F), −139.27 (d, $^3J_{F-F}$=20.3 Hz, 3 F), −139.67 (t, $^3J_{F-F}$=25.1 Hz, 6F), −155.73 (t, $^3J_{F-F}$=20.9 Hz, 3 F), −160.91 (s, br, 3 F), −163.25 (t, $^3J_{F-F}$=21.7 Hz, 3F), −163.56 (t, $^3J_{F-F}$=22.0 Hz, 3 F), −164.13 (t, $^3J_{F-F}$=21.4 Hz, 3 F). Anal Calcd for C$_{80}$H$_{72}$BF$_{27}$Zr$_2$: C, 55.23; H, 4.17; N, 0.00. Found: C, 54.81; H, 3.98; N, 0.00.

EXAMPLE 6

Synthesis of [Cp$_2$M(H)(μ-H)(H)ZrCp$_2$]$^⊕$[MePBB]$^⊖$; (M=Zr; Cp=C$_5$H$_5$ or C$_5$H$_3$Me$_2$)

The procedure here is similar to that of Example 5, except that the reaction was carried out under 1 atm of H$_2$ for 15 h: yields 81.6% (Cp=C$_5$H$_5$, grey solid) and 75.6% (Cp=C$_5$H$_3$Me$_2$, orange solid). Analytical and spectroscopic data for Cp=C$_5$H$_5$ are as follows. $^1$H NMR (C$_6$D$_6$, 58° C.): δ6.67 (s, br, 2 H, Zr—H), 5.64 (s, 20 H, C$_5$H$_5$),−0.81 (s, br, 3 H, B—CH$_3$), −1.38 (s, br, 1 H, Zr—H—Zr). The chemical shifts and splitting patterns of $^{19}$F NMR are same as those of Example 5 (Cp=C$_5$H$_5$). Anal. Calcd. for C$_{57}$H$_{26}$BF$_{27}$Zr$_2$: C, 48.31; H, 1.85; N, 0.00. Found: C, 47.90; H, 1.92; N, 0.00.

Analytical and spectroscopic data for Cp=C$_5$H$_3$Me$_2$ are as follows. $^1$H NMR (C$_7$D$_8$, 23° C.): δ5.81 (m, 4 H, C$_5$H$_3$Me$_2$), 5.50 (m, 4 H, C$_5$H$_3$Me$_2$), 523 (m, 4 H C$_5$H$_3$Me$_2$). 1.65 (m, 24 H, C$_5$H$_3$Me$_2$), 0.25 (s, br, 2 H, Zr—H), −0.94 (s, br, 3 H, B—CH$_3$), −1.52 (s, br, I H, Zr—H—Zr). The chemical shifts and splitting patterns of $^{19}$F NMR are same as those of Example 5 (Cp=C$_5$H$_3$Me$_2$).

Anal. Calcd for C$_{65}$H$_{42}$BF$_{27}$Zr$_2$: C, 51.05; H, 2.77; N, 0.00 Found C, 51.07; H. −2.63; N. 0.00.

EXAMPLE 7

Synthesis of [Cp$_2$MMe]$^⊕$[MePBB]$^⊖$(M=Zr; Cp=C$_5$H$_5$, C$_5$H$_3$Me$_2$, or C$_5$Me$_5$)

7(a) Cp=C$_5$H$_5$. In a J-Young NMR tube, a small amount of a mixture of (C$_5$H5)$_2$ZrMe$_2$ and PBB (1:1.2 molar ratio) was dissolved in C$_6$D$_6$). The NMR tube was then put in an NMR probe and heated at 60° C. After 0.5 h, $^1$H NMR revealed the above monomeric species formed. The same structure was obtained by the reaction of the C$_5$H$_5$ product of Example 5 with an excess of PBB at 60° C. for 0.5 h. In a polymerization test, these species were also generated in situ by mixing (C$_5$H$_5$)$_2$ZrMe$_2$ and PBB at 60° C. for 0.5 h. $^1$H NMR (C$_6$D$_6$, 60° C.) for: δ5.70 (s, 10 H, C$_5$H$_5$), 0.14 (s, 3 H, Zr—CH$_3$), −0.85 (s, br, 3 H, B—CH$_3$). $^{19}$F NMR is similar to that of the corresponding dinuclear species of Example 5 (Cp=C$_5$H$_5$).

7(b) Cp=C$_5$H$_3$Me$_2$). The same procedure of Example 5(a) was used to prepare this species. In the polymerization test, the following was observed: $^1$H NMR (C$_7$D$_8$, 60° C.) for 8: δ5.68 (t, 3 J H-H=2.8 Hz, 4 H, C$_5$H$_3$M$_2$), 5.36 (t, $^3J_{H-H}$=3.1 Hz, 4 H, C$_5$H$_3$Me$_2$), 5.23 (t, $^3$JH-H=2.8 Hz, 4 H, C$_5$H$_3$Me$_2$). 1.76 (s, 6 H, C$_5$H$_3$Me$_2$), 1.56 (s, 6 H, C$_5$H$_3$Me$_2$), 0.17 (s, 3 H, Zr—CH$_3$), −0.93 (s, br, 3 H, B—CH$_3$). $^{19}$F NMR of this species is similar to that of the corresponding dinuclear species of Example 5 (Cp=C$_5$Me$_5$). $^{13}$C NMR (C$_7$D$_8$, 60° C.): δ117.74 (C$_5$H$_3$Me$_2$), 112.14 (C$_5$H$_3$Me$_2$), 108.01 (C$_5$H$_3$Me$_2$), 42.11 (Zr—CH$_3$), 34.43 (B—CH$_3$), 12.63 (C$_5$H$_2$Me$_2$), 12.45 (C$_5$H$_2$Me$_2$).

7(c) Cp=C$_5$Me$_5$. The same procedure of Example 5(a) was used to prepare this species. In the polymerization test, the following was observed: $^1$H NMR (C$_6$D$_6$, 60° C.): δ1.61 (s, 30 H, C$_5$Me5), 0.13 (s, 3 H, Zr—CH$_3$), −0.86 (s, br, 3 H, B—CH$_3$). $^{19}$F NMR is similar to that of the corresponding dinuclear species of Example 5, Cp=C$_5$Me$_5$.

EXAMPLE 8

Synthesis of [CpM(Me)$_2$]$^⊕$[MePBB]$^⊖$(M=Ti; Cp=C$_5$Me$_5$)

The catalyst product of FIG. 5 was generated in an NMR tube reaction by mixing C$_5$Me$_5$TiMe$_3$ and PBB at 1:1 molar ratio in C$_6$D$_6$ for 2 h. $^1$H NMR (C$_6$D$_6$, 23° C.) δ9.03 (s, br, 2 H. CH$_2$), 1.69 (s, 6 H, C$_5$Me$_4$), 1.65 (s, 6 H, C$_5$Me$_4$), 0.15 (s, 3 H, Ti—CH$_3$), −0.82 (s, br, 3 H, B—CH$_3$).

EXAMPLE 9

Synthesis of {[Me$_2$Si($^t$BuN)(C$_5$Me$_4$)]MMe}$^⊕$[MePBB]$^⊖$(M=Zr or Ti)

9(a) M=Zr. [Me$_2$Si($^t$BuN)(C$_5$Me$_4$)]ZrMe$_2$ (0.199 mmol) and PBB (0.199 mmol) were treated in the same way as in the synthesis of Example 3 except that here the reaction time was 2 hours. This procedure yielded 73.1% of {[Me$_2$Si ($^t$BuN)(C$_5$Me$_4$)]ZrMe}$^⊕$[MePBB]$^⊖$(yellow solid). Analytical and spectroscopic data are as follows. $^1$H NMR (C$_7$D$_8$, 23° C.): δ1.73 (s, 3 H, C$_5$Me$_4$), 1.69 (s, 3 H, (C$_5$Me$_4$), 1.63 (s, 3 H, C$_5$Me$_4$), 1.43 (s, 3 H, C$_5$Me$_4$), 0.85 (s, 9 H, N—tBu), 0.28 (s, 3 H, SiMe$_2$), 0.21 (s, 3 H, SiMe$_2$), −0.48 (s, 3 H, Zr—CH$_3$), −0.95 (s, br, 3 H, B—CH$_3$). $^{19}$F NMR (C$_7$D$_8$, 23° C.): δ−124.20 (s, br, 3 F), −139.14 (d, $^3J_{F-F}$=23.7 Hz, 3 F), −139.35 (d, $^3J_{F-F}$=22.0 Hz, 3 F), −139.93 (d, $^3J_{F-F}$=21.2 Hz, 3 F), −155.79 (t, $^3J_{F-F}$=21.2 Hz, 3 F), −159.67 (t, $^3J_{F-F}$=22.3

Hz, 3 F), −163.28 (t, $^3J_{F-F}$=21.7 Hz, 3 F), −163.87 (t, $^3J_{F-F}$=22.6 Hz, 3 F), −164.13 (t, $^3J_{F-F}$=22.6 Hz, 3 F). $^{13}$C NMR (C$_7$D$_8$, 23° C.): δ130.22 (C$_5$Me$_4$), 128.18 (C$_5$Me$_4$), 127.22 (C$_5$Me$_4$), 126.47 (C$_5$Me$_4$), 124.37 (C$_5$Me$_4$), 58.47 (N—CMe$_3$), 34.37 (Zr—CH$_3$), 34.10 (N—CMe$_3$), 15.89 (C$_5$Me$_4$), 13.46 (C$_5$Me4), 11.77 (C$_5$Me$_4$), 10.99 (C$_5$Me$_4$), 7.92 (SiMe$_2$), 5.65 (SiMe$_2$). Anal. Calcd for C$_{53}$H$_{33}$BF$_{27}$NSiZr: C, 47.97; H, 2.51; N, 1.06, Found: C, 47.79; H, 2.58; N, 0.86.

9(b) M =Ti. The procedure of 9(a) was repeated using [Me$_2$Si($^t$BuN)(C$_5$Me$_4$)]TiMe$_2$ but with a reaction time of 4 hours instead of 2 hours. This procedure yielded 47.0% of {[Me$_2$Si($^t$BuN)(C$_5$Me$_4$)]TiMe}$^⊕$[MePBB]$^⊖$(orange solid). The spectroscopic data are similar to those of 9(a) above.

EXAMPLE 10

Synthesis of [CpM(Me)$_2$]$^⊕$[MEPBB]$^⊖$(M=Zr or Hf; Cp=C$_5$Me$_5$)

C$_5$Me$_5$MMe$_3$ (0.199 mmol) and PBB (0.191 g, 0.199 mmol) were treated in the same manner as in Example 3 to produce 0.174 g of [C$_5$Me$_5$Zr(Me)$_2$]$^⊕$[MePBB]$^⊖$ and 0.144 g of [C$_5$Me$_5$Hf(Me)$_2$]$^⊕$[MePBB]$^⊖$ as yellow solids in yields of 69.1% and 43.6%, respectively. An NMR reaction showed that a quantitative yield of these complexes was achieved if isolation of the product is not required. Analytical and spectroscopic data for [C$_5$Me$_5$Zr(Me)$_2$]$^⊕$[MePBB]$^⊖$ are as follows. $^1$H NMR (C$_7$D$_8$, 23° C.): δ7.14 (s, 3 H, ½ C$_6$H$_6$), 1.40 (s, 15 H, (C$_5$Me$_5$), −0.60 (s, 6 H, Zr—CH$_3$), −0.95 (s, br, 3 H, B—CH$_3$). $^{19}$F NMR (C$_7$D$_8$, 23° C.): δ−124.21 (d, $^3J_{F-F}$=21.5 Hz, 3 F), −139.06 (t, $^3J_{F-F}$=24.5 Hz, 6 F), −140.10 (d, $^3J_{F-F}$=23.7 Hz, 3 F) −155.42 (t, $^3J_{F-F}$=20.9 Hz, 3 F), −159.66 (s, br, 3 F), −163.14 (t, $^3J_{F-F}$=21.5 Hz, 3 F), −163.54 (t, $^3J_{F-F}$=24.5 Hz, 3 F), −163.93 (t, $^3J_{F-F}$=21.7 Hz, 3 F). $^{13}$C NMR (C$_7$D$_8$, 23° C.): δ128.29 (d, $^1J_{C-H}$=158.2 Hz, C$_6$H$_6$), 123.13 (s, C$_5$Me$_5$), 45.07 (q, $^1J_{C-H}$=119.8 Hz, Zr—CH$_3$), 11.31 (q, $^1J_{C-H}$=127.38 Hz, C$_5$Me$_5$). Anal. Calcd. for C$_{49}$H$_{24}$BF$_{27}$Zr.½C$_6$H$_6$: C, 49.30; H, 2.15. Found: C, 49.18; H, 2.07. Analytical and spectroscopic data for [C$_5$Me$_5$Hf(Me)$_2$]$^⊕$[MePBB]$^⊖$ are as follows. $^1$H NMR (C$_7$D$_8$, 23° C.): δ7.14 (s, 1.5 H, ¼ C$_6$H6), 1.46 (s, 15 H, C$_5$Me$_5$), −0.84 (s, 6 H, Hf—CH$_3$), −0.95 (s, br, 3 H, B—CH$_3$). $^{19}$F NMR (C$_6$D$_6$, 23° C.): δ−124.14 (d, $^3J_{F-F}$=21.4 Hz, 3 F), −139.29 (t, $^3J_{F-F}$=22.6 Hz, 6 F), −140.12 (d, $^3J_{F-F}$=24.5 Hz, 3 F), −155.52 (t, $^3J_{F-F}$=21.4 Hz, 3 F), −159.69 (t, $^3J_{F-F}$=22.6 Hz, 3 F), −162.91 (t, $^3J_{F-F}$=21.4 Hz, 3 F), −163.49 (t, $^3J_{F-F}$=23.1 Hz, 3 F), −164.00 (t, $^3J_{F-F}$=22.3 Hz, 3 F). $^{13}$C NMR (C$_{66}$, 23° C.); δ124.89 (C$_5$Me$_5$), 49.59 (Hf—Me), 11.07 (C$_5$Me$_5$), 10.85 (B—Me). Anal. Calcd for C$_{49}$H$_{24}$BF$_{27}$Hf.¼C$_6$H$_6$: C, 45.5; H, 1.93. Found: C, 45.16; H, 2.08.

EXAMPLE 11

In Situ Generation of {[rac-Me$_2$Si(Ind)$_2$MMe]$_2$($μ$-Me)}$^⊕$[MePBB]$^⊕$(M=Zr)

rac-Me$_2$Si(Ind)$_2$ZrMe$_2$ (8.2 mg, 0.020 mmol) and PBB (9.6 mg, 0.010 mmol) were loaded into a J-Young NMR tube and benzene-d$_6$ was condensed in. The mixture was allowed to react at room temperature for 1 h before the NMR spectrum was recorded. A pair of diastereomers was formed in a 2:1 ratio. $^1$H NMR (C$_6$D$_6$, 23° C.) for diastereomer A: δ7.30–6.78 (m, 16 H, C$_6$H$_4$), 5.68 (D, J$_{H-H}$=2.5 Hz, 4 H, C$_5$H$_2$), 5.31 (d, J$_{H-H}$=2.5 Hz, 4 H, C$_5$H$_2$), 0.68 (s, 6 H, SiMe$_2$), 0.47 (s, 6 H, SiMe$_2$), −0.83 (s, br, 3 H, B—CH$_3$), −0.92 (s, δH, Zr—CH$_3$), −2.87 (s, 3 H, Zr—CH$_3$—Zr).

Diastereomer B: δ7.30–6.78 (m, 16 H, C$_6$H$_4$), 6.59 (d, J$_{H-H}$=2.5 Hz, 4 H, C$_5$H$_2$), 5.93 (d, J$_{H-H}$=2.5 Hz, 4 H, C$_5$H$_2$), 0.67 (s, 6 H, SiMe$_2$), 0.44 (s, 6 H, SiMe$_2$), −0.83 (s, br, 3 H, B—CH$_3$), 0.96 (s, 6 H, Zr—CH$_3$), −3,07 (s, 3 H, Zr—CH$_3$—Zr). $^{19}$F NMR (C$_6$D$_6$, 23° C.: δ−123.00 (d, $^3J_{F-F}$=17.5 Hz, 3 F), −139.28 (m, 6 F), −140.09 (d, $^3J_{F-F}$=21.5 Hz, 3 F), −156.02 (t, $^3J_{F-F}$=20.9 Hz, 3 F), −159.90 (t, $^3J_{F-F}$=22.3 Hz, 3F), −163.26 (t, $^3J_{F-F}$=22.3 Hz, 3F), −163.67 (t, $^3J_{F-F}$=22.5 Hz, 3 F), −164.20 (t, $^3J_{F-F}$=22.6 Hz, 3 F).

EXAMPLE 12

Synthesis of {[Me$_2$C(Flu)(Cp)MMe]$_2$($μ$-Me)}$^⊕$ [MePBB]$^⊕$(M=Zr)

In a glovebox, Me$_2$C(Flu)(Cp)ZrMe$_2$ (39.2 mg, 0.100 mmol) and PBB (47.8 mg, 0.050 mmol) were loaded into a 25-mL reaction flask having filter frit and the flask was reattached to the high vacuum line. Benzene (20 mL) was then vacuum-transferred into the flask at −78° C. The mixture was slowly allowed to warm to room temperature and stirred for an additional 2 hours. The solvent was removed in vacuo, and pentane (20 mL) was condensed into the flask. The resulting suspension was filtered, and the collected solid was washed with 5 mL of pentane and dried under vacuum to afford 73.9 mg of the title complex, yield 80.5%. Two diastereomers are formed in a 1.8 (isomer A):1 (isomer B) ratio. $^1$H NMR (C$_7$D$_8$, 23° C.) for diastereomer A: δ7.52 (t, J$_{H-H}$=7.2 Hz 4 H, C$_6$H$_4$), 7.30 (t, J$_{H-H}$=7.2 Hz, 4H, C$_6$H$_4$), 7.10 (t, J$_{H-H}$=7.2 Hz, 4 H, C$_6$H$_4$), 7.09–6.86 (m, 6H, C$_6$H$_4$), 6.23 (d, J$_{H-H}$=2.4 Hz, 2H, C$_5$H$_4$), 5.49 (d, J$_{H-H}$=2.4 Hz, 2 H, C$_5$H$_4$), 5.17 (d, J$_{H-H}$=2.4 Hz, 2 H, C$_5$H$_4$), 4.88 (d, J$_{H-H}$=2.4 Hz, 2 H, C$_5$H$_4$), 1.76 (s, 6 H, CMe$_2$), 1.62 (s, 6 H, CMe$_2$), −0.91 (s, br, 3 H, B—CH$_3$), −1.21 (s, 6 H, Zr—CH$_3$), −3.38 (s, 3 H, Zr—CH$_3$—Zr). Isomer B δ7.71 (d, J$_{H-H}$=8.4 Hz, 4 H, C$_6$H$_4$), 7.61 (d, J$_{H-H}$=8.4 Hz, 4 H, C$_6$H$_4$), 7.23 (t, J$_{H-H}$=7.2 Hz, 4 H, C$_6$H$_4$), 7.09–6.86 (m, 6 H, C$_6$H$_4$), 6.17 (d, J$_{H-H}$=2.4 Hz, 2 H, C$_5$H$_4$), 5.51 (d, J$_{H-H}$=2.4 Hz, 2 H, C$_5$H$_4$), 5.08 (d, J$_{H-H}$=2.4 Hz, 2 H, C$_5$H$_4$), 4.78 (d, J$_{H-H}$=2.4 Hz, 2 H, C$_5$H$_4$), 1.78 (s, 6 H, CMe$_2$), 1.62 (s, 6 H, CMe$_2$), −0.91 (s, br, 3 H, B—CH$_3$), −1.27 (s, 6 H, Zr—CH$_3$), −3.29 (s, 3 H, Zr—CH$_3$—Zr). $^{19}$F NMR (C$_7$D$_8$, 23° C.): δ−123.56 (s, br, 3 F), −138.86 (d, $^3J_{F-F}$=23.9 Hz, 3 F), −139.45 (d, $^3J_{F-F}$=21.4 Hz, 3 F), −139.74 (d, $^3J_{F-F}$=21.5 Hz, 3 F), −156.79 (t, $^3J_{F-F}$=20.9 Hz, 3 F), −159.94 (t, J$_{F-F}$=22.6 Hz, 3 F), −163.20 (t, $^3J_{F-F}$=20.9 Hz, 3 F), −163.75 (t, $^3J_{F-F}$=22.5 Hz, 3 F), −164.14 (t, $^3J_{F-F}$=22.6 Hz, 3 F). Anal. Calcd for C$_{82}$H$_{48}$BF$_{27}$Zr$_2$: C, 56.62; H, 2.78. Found: C, 55.80; H, 2.10.

EXAMPLE 13

Conversion of [Cp$_2$M(Me)($μ$-Me)(Me)MCp$_2$]$^⊕$ [MePBB]$^⊖$ to [Cp$_2$M(Me)($μ$-F)(Me)MCp$_2$]$^⊖$ [MePBB]$^⊖$(M=Zr; C$_5$H$_3$Me$_2$)

Upon standing at 25° C. for four days or at 80° C. for 1 hour, a solution of [(C$_5$H$_3$Me$_2$)$_2$Zr(Me)($μ$-Me)(Me)Zr (C$_5$H$_3$Me$_2$)$_2$]$^⊕$ [MePBB]$^⊖$ in C$_7$D$_8$ decomposed to yield [(C$_5$H$_3$Me$_2$)$_2$Zr(Me)($μ$-F)(Me)Zr(C$_5$H$_3$Me$_2$)$_2$]$^⊕$[MePBB]$^⊖$, which was characterized both spectroscopically and analytically from a scale-up synthesis in toluene. $^1$H NMR (C$_7$D$_8$, 23° C.): δ5.68 (t, $^3J_{H-H}$=2.8 Hz, 4 H, C$_5$H$_3$Me$_2$), 5.36 (t, $^3J_{H-H}$=3.1 Hz, 4 H, C$_5$H$_3$Me$_2$), 5.23 (t, $^3J_{H-H}$=2.8 Hz, 4 H, C$_5$H$_3$Me$_2$), 1.71 (s, 12 H, C$_5$H$_3$Me$_2$), 1.43 (s, 12 H, C$_5$H$_3$Me$_2$), 0.12 (d, $^3J_{H-F}$=2.1 Hz, 6 H, Zr—CH$_3$), −0.92 (s, br, 3 H, B—CH$_3$). $^{19}$F NMR spectrum is the same as that of [(C$_5$H$_3$Me$_2$)$_2$Zr(Me)($μ$-Me)(Me)Zr(C$_5$H$_3$Me$_2$)$_2$]$^⊕$ [MePBB]$^⊖$ except there is an extra peak at −91.27 ppm (s)

for the bridging F signal. $^{13}$C NMR (C$_7$D$_8$, 23° C.): δ117.74 (C$_5$H$_3$Me$_2$), 114.33 (C$_5$H$_3$Me$_2$), 112.14 (C$_5$H$_3$Me$_2$), 111.45 (C$_5$H$_3$Me$_2$), 108.01 (C$_5$H$_3$Me$_2$), 42.11 (Zr—CH$_3$), 34.43 (B—CH$_3$), 12.63 (C$_5$H$_3$Me$_2$), 12.45 (C$_5$H$_3$Me$_2$). Anal. Calcd for C$_{67}$H$_{45}$BF$_{28}$Zr$_2$: C, 51.09; H, 2.88. Found: C, 50.71; H, 2.61.

EXAMPLE 14

Synthesis of Cp$_2$MMe$^\oplus$[(C$_6$F$_5$)$_2$B(C$_{12}$F$_9$)Me] $^\ominus$M═Zr; Cp═C$_5$H$_5$)

(C$_5$H$_5$)$_2$ZrMe$_2$ (50 mg, 0.21 mmol) and (C$_6$F$_5$)$_2$B(C$_{12}$F$_9$) (146 mg, 0.22 mmol) were loaded into a 25-mL reaction flask in a glove box. On the high vacuum line, C$_6$H$_6$ (15 mL) was condensed in at −78° C. The solution was then stirred at room temperature for 1 h, and all the volatiles were removed under high vacuum to give a yellow solid. Pentane was condensed in to wash the solid twice, and the yellow solid was dried under vacuum (10$^{-5}$ torr) for 4 h at room temperature. Yield, 110 mg (61%). The spectroscopic data for (C$_5$H$_5$)$_2$ZrMe$^\oplus$[(C$_6$F$_5$)$_2$B(C$_{12}$F$_9$)Me]$^\ominus$ are as follows. $^1$H NMR (benzene-d$_6$, 299.91 MHz, 23° C.) δ5.47 (s, 10 H, C$_5$H5), 0.32 (s, 3H, ZrCH$_3$), 0.24 (br, 3 H, BCH$_3$). $^{13}$C NMR (benzene-d$_6$, 74.42 MHz, 23° C.) δ114.04 (C$_5$H$_5$), 40.92 (ZrCH$_3$), $^{19}$F NMR (benzene-d$_6$, 282.33 MHz, 23° C.) δ−128.75 (s, 1 F, 3-F), −132 (very broad, 4 F, o-F), −136.80 (s, 1 F, 6-F), −138.94 (s, 2 F, 2', 6'-F), −153.48 (t, $^3J_{F-F}$=21.1 Hz, 1 F, 4'-F), −156.46 (t, $^3J_{F-F}$=22.2 Hz, 1 F, 4-F), −158.41 (multi, 3 F, p-F, 5-F), −162.91 (s, 2 F, 3', 5'-F), −164.00 (br, 4 F, m-F), Anal. Calcd. for C$_{36}$H$_{16}$BF$_{19}$Zr; C, 47.44; H, 1.76. Found: C, 47.09, H, 1.67.

EXAMPLE 15

Synthesis of rac-Me$_2$Si(Cp)$_2$MMe$^\oplus$[(C$_6$F$_5$)$_2$B (C$_{12}$F$_9$)Me]$^\ominus$ (M═Zr; Cp═C9H$_7$)

rac-Me$_2$Si(Ind)$_2$ZrMe$_2$ (50 mg, 0.13 mmol) and (C$_6$F$_5$)$_2$B(C$_{12}$F$_9$)(87 mg, 0.13 mmol) were loaded into a 25-mL reaction flask in a glove box. On the high vacuum line, C$_6$H$_6$(10 mL) was condensed in at −78° C. The solution was then stirred at room temperature for 1 h, and all of the volatiles were removed under high vacuum to give a yellow solid. Pentane was condensed in to wash the solid twice, and the yellow solid was dried under vacuum (10$^{-5}$ torr) for 4 h at room temperature. Yield, 82 mg (60%). The spectroscopic data for rac-Me$_2$Si(Ind)$_2$ZrMeD$^\oplus$[(C$_6$F$_5$)$_2$B(C$_{12}$F$_9$)Me]$^\ominus$ are as follows. $^1$H NMR (C$_6$D$_6$, 23° C., 399.941 MHz): δ7.63 (d, $^3J_{H-H}$=8.5 Hz, 1 H, Ind), 7.26 (d, $^3J_{H-H}$=8.5 Hz, 1 H, Ind). 7.06 (t, $^3J_{H-H}$=7.4 Hz, 1 H, Ind), 6.99 (d, $^3J_{H-H}$=8.4 Hz, 1 H, Ind), 6.62–6.72 (m, 2 H, Ind), 6.58 (d, $^3J_{H-H}$=3.0 Hz, 1 H, Ind), 6.54 (d, $^3J_{H-H}$=7.8 Hz, 1 H, Ind), 6.26 (d, 1 H $^3J_{H-H}$=8.1 Hz, Ind), 6.21 (d, 1 H $^3J_{H-H}$=3.0 Hz, Ind), 5.65 (d, 1 H $^3J_{H-H}$=3.3 Hz, Ind), 4.95 (d, 1 H $^3J_{H-H}$=−3.3 Hz, Ind), 0.36 (s, 3 H, Me$_2$Si), 0.21 (s, 3 H, Me$_2$Si), −0.32 (s, br, 3 H, B—CH$_3$), −0.55 (s, 3 H, Zr—CH$_3$). $^{19}$F NMR (benzene-d$_6$, 282.33 MHz, 23° C.) δ−127.53 (s, 1 F, 3-F), −131 (very broad, 4 F, o-F), −137.15 (m, 1 F, 6-F), −137.94 (m, 2 F, 2', 6'-F), −153.74 (t, $^3J_{F-F}$=21 Hz, 1 F, 4'-F), −156.65 (t, $^3J_{F-F}$=22 Hz, 1 F, 4-F) −158.56 (m, 2 F, p-F), −159.26 (t, $^3J_{F-F}$=21 Hz, 1 F, 5-F), −162.75 (br, 1 F, 3'/5'-F), −163 (br, 1 F, 3'/5'-F), −164.16 (br, 4 F, m-F). Anal. Calcd. for C$_{46}$H$_{24}$BF$_{19}$Zr: C, 53.14; H, 2.33. Found: C, 52.82, H, 2.37.

EXAMPLE 16

Synthesis of {[Me$_2$Si($^t$BuN)(C$_5$Me$_4$)]MMe}$^\oplus$ [(C$_6$F$_5$)$_2$B(C$_{12}$F$_9$)Me]$^\ominus$(M═Zr)

CGCZrMe$_2$ (80 mg, 0.22 mmol) (C$_6$F$_5$)$_2$B(C$_{12}$F$_9$)(142 mg, 0.22 mmol) were loaded into a 25 mL reaction flask in the glove box. On the high vacuum line C$_6$H$_6$ (15 mL) was condensed in at −78° C. The solution was then stirred at room temperature for 1 h, and all the volatiles were removed under high vacuum to give a yellow solid. Pentane was condensed in to wash the solid twice, and the yellow solid was dried under vacuum (10$^{-5}$ torr) for 4 hours at room temperature. Yield, 119 mg (53%). The spectroscopic data for {[Me$_2$Si($^t$BuN)(C$_5$Me$_4$)]MMe}$^\oplus$[(C$_6$F$_5$)$_2$B(C$_{12}$F$_9$) Me]$^\ominus$ are as follows. $^1$H NMR (benzene-d$_6$, 299.91 MHz, 23° C.) δ1.73 (s, 3 H, CH$_3$), 1.68 (s, 3 H, CH$_3$), 1.59 (s, 3 H, CH$_3$), 1.46 (s, CH$_3$), 146 (s, 3 H, CH$_3$), 1.00 (s, 12 H, CMe$_3$/BCH$_3$), 0.31 (s, 3 H, ZrCH$_3$), 0.24 (s, 3 H, SiCH$_3$), 0.17 (s, 3 H, SiCH$_3$), $^{13}$C NMR (benzene-d$_6$, 74.42 MHz, 23° C.) δ57.74 (ZrCH$_3$), 44.27 (CMe$_3$), 33.05 (CMe$_3$), 15.04 (CH$_3$), 12.74 (CH$_3$), 11.37 (CH$_3$), 10.37 (CH$_3$), 5.54 (SiCH$_3$), 5.12 (SiCH$_3$), $^{19}$F NMR (benzene-d$_6$, 282.33 MHz, 23° C.) δ−129.31 (s, 1 F, 3-F), −131.67 (br, 4 F, o-F), −136.49 (s, 1 F, 6-F), −138.38 (s, 2 F, 2', 6'-F), −153.48 (t, $^3J_{F-F}$=21.3 Hz, 1 F, 4'-F), −156.02 (t, $^3J_{F-F}$=21.5 Hz, 1 F, 4-F), −158.42 (s, 3 F, p-F, 5-F), −162.99 (s, 2 F, 3', 5'-F), −163.89 (br, 4 F, m-F). Anal. Calcd. for C$_{41}$H$_{33}$BF$_{19}$NSiZr: C, 47.77; H, 3.22. Found: C, 47.10, H, 3.01.

EXAMPLE 17

Synthesis of {[Me$_2$Si($^t$BuN)(C$_5$Me$_4$)]MMe}$^\oplus$ [(C$_6$F$_{\%}$)$_2$B(C$_{12}$F$_9$)Me]$^\ominus$ (M═Ti)

CGCTiMe$_2$ (70 mg, 0.21 mmol) and (C$_6$F$_5$)$_2$B(C$_{12}$F$_9$) (141 mg, 0.21 mmol) were loaded into a 25 mL reaction flask in the glove box. On the high vacuum line C$_6$H$_6$ (15 mL) was condensed in at −78° C. The solution was then stirred at room temperature for 1 hour, and all the volatiles were removed under high vacuum to give a yellow solid. Pentane was condensed in to was the solid twice, and the yellow solid was dried under vacuum (10$^{-5}$ torr) for 4 hours at room temperature. Yield, 101 mg (48%). The spectroscopic data for {[Me$_2$Si($^t$BuN)(C$_5$Me$_4$)]MMe}$^\oplus$[(C$_6$F$_{\%}$)$_2$B (C$_{12}$F$_9$)Me]$^\ominus$ are as follows. $^1$H NMR (benzene-d$_6$, 299.91 MHz, 23° C.) δ1.71 (s, 3 H, CH$_3$), 1.54 (s, 3 H, CH$_3$), 1.53 (s, 3 H, CH$_3$), 1.41 (s, 3 H, CH$_3$), 0.99 (s, 9 H, CMe$_3$), 0.95 (s, 3 H, TiCH$_3$), 0.66 (br, 3 H, BCH$_3$), 0.29 (s, 3 H, SiCH$_3$), 0.16 (s, 3 H, SiCH$_3$), $^{19}$F NMR (benzene-d$_6$, 282.33 MHz, 23° C.) δ−126.96 (s, 1 F, 3-F), 131.04 (br, 4 F, o-F), −136.85 (m, 1 F, 6-F), −138.10 (s, 2 F, 2', 6'-F), −153.60 (t, $^3J_{F-F}$=21 Hz, 1 F, 4'-F), −156.26 ($^3J_{F-F}$=22 Hz, 1 F, 4-F), −158.44 −158.75 (m, 2 F, p-F), −158.84 (t, $^3J_{F-F}$=22 Hz, 1 F, 5-F), −162.90 (s, 1 F, 3'/5'-F), −163.34 (s, 1 F, 3'/5'-F), −164.12 (br, 4 F, m-F). Anal. Calcd. for C$_{41}$H$_{33}$BF$_{19}$NSiTi: C, 49.87; H, 3.37. Found: C, 49.89, H, 3.43.

Analogous catalytic complexes of this invention are formed when Examples 3–17 are repeated using chemically equivalent amounts of organoboranes of formula (I), or organoboranes of formula (II), or of formula (III), in place of the organoboranes used in Examples 3–17.

Polymerization Reactions and Supported Cocatalysts of this Invention

The catalytic complexes of this invention are effective for use as catalysts for producing a variety of homopolymers and copolymers. When employed as catalysts, the catalytic complexes of this invention can be used in solution or deposited on a solid support. When used in solution polymerization, the solvent can be, where applicable, a large excess quantity of the liquid olefinic monomer. Typically, however, an ancillary inert solvent, typically a liquid paraffinic or aromatic hydrocarbon solvent is used, such as heptane, isooctane, decane, toluene, xylene, ethylbenzene, mesitylene, or mixtures of liquid paraffinic hydrocarbons and/or liquid aromatic hydrocarbons. When the catalytic complexes of this invention are supported on a carrier, the solid support or carrier can be any suitable particulate solid, and particularly a porous support such as talc, one or more zeolites, or one or more inorganic oxides, or a resinous support material such as a polyolefin. Preferably, the support material is an inorganic oxide in finely divided form.

Suitable inorganic oxide support materials which are desirably employed include metal oxides such as silica, alumina, silica-alumina and mixtures thereof. Other inorganic oxides that may be employed either alone or in combination with the silica, alumina or silica-alumina are magnesia, titania, zirconia, and like metal oxides. Such support materials can be treated with a suitable reagent such as an alumoxane (e.g., methylalumoxane) or an alkylaluminum compound (e.g., an aluminum trialkyl such as triethylaluminum). Other suitable support materials are finely divided polyolefins such as finely divided polyethylene.

In a preferred embodiment of this invention there is provided a supported cocatalyst composition comprising an organoborane of formula (I), formula (II), or formula (III) above supported on a carrier such as described above, and especially on a porous support such as talc, a zeolite, or one or inorganic oxides, most preferably a porous silica. Such compositions are of advantage in that such supported cocatalysts can be provided to various end users for carrying out polymerization reactions using their own respective preferred d- or f-block metal-containing catalyst. All that is required is for the end user to contact the selected d- or f-block metal-containing compound having at least one leaving group with the supported organoborane composition of this invention in the presence of a suitable solvent or diluent so that the catalytic complex is formed on and/or in the pores of the support, thereby forming a supported catalyst of this invention.

Another preferred embodiment of this invention is a supported catalyst composition comprising a catalytic complex of this invention formed from d- or f-block metal-containing compound having at least one leaving group, and an organoborane of formula (I), formula (II), or formula (III) above, supported on a carrier such as described above, and especially on a porous support such as talc, a zeolite, or one or more inorganic oxides, most preferably a porous silica.

In preparing the supported organoborane cocatalysts of this invention, the organoborane of this invention can be added to and mixed with a slurry of the support in a suitable anhydrous inert liquid diluent so that the cocatalyst is deposited on the support. Agitation and heat can be utilized in performing this operation. After the deposition has occurred, the treated support is isolated and dried under an inert atmosphere to prepare a supported cocatalyst of this invention. Such supported dried cocatalyst should be kept under an inert atmosphere or in an anhydrous inert diluent under an inert atmosphere until the use of the supported cocatalyst in forming an active catalyst composition, a step which typically will be conducted in situ immediately prior to initiation of a polymerization reaction pursuant to this invention. Another preferred way of forming the supported organoborane cocatalyst compositions of this invention is to employ the incipient impregnation technique described in U.S. Pat. Nos. 5,332,706 and 5,473,028. In utilizing this technique, a supported catalyst is formed by contacting a porous silica having a known total pore volume with a solution of an organoborane of formula (I), (II), or (III) above, the volume of the solution being equal to or less than such total pore volume so that the solution impregnates the silica and is thus disposed within the body of the resultant dry particles. In U.S. Pat. No. 5,602,067 this concept is expanded to using an even larger volume of the solution, provided the volume of the solution is less than required for forming a slurry of the catalyst particles in the solution, and this procedure can be adapted for use with the organoboranes of formulas (I), (II), and (III) above in lieu of the aluminoxanes referred to in the patent.

To prepare the supported catalyst compositions of this invention, the procedures described in the immediately preceding paragraph can be utilized with the exception that in addition to an organoborane of formula (I), (II), or (III) above, a d- or f-block metal compound having at least one leaving group is used so that the metal compound and the organoborane interact with each other to produce the active catalytic complex which is supported on and/or in the pores of the support. Thus use can be made of any catalyst slurry deposition procedure, or the incipient impregnation procedures of U.S. Pat. Nos. 5,332,706 and 5,473,028, or the procedure of U.S. Pat. No. 5,602,067 involving use of a volume of treating solution in excess of the total pore volume but less than the volume required for forming a slurry of the catalyst particles in the solution of the catalyst.

Polymers can be produced pursuant to this invention by homopolymerization of polymerizable olefins, typically 1-olefins (also known as α-olefins) such as ethylene, propylene, 1-butene, styrene, or copolymerization of two or more copolymerizable monomers, at least one of which is typically a 1-olefin. The other monomer(s) used in forming such copolymers can be one or more different 1-olefins and/or a diolefin, and/or a polymerizable acetylenic monomer. Olefins that can be polymerized in the presence of the catalysts of this invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Normally, the hydrocarbon monomers used, such as 1-olefins, diolefins and/or acetylene monomers, will contain up to about 10 carbon atoms per molecule. Preferred 1- olefin monomers for use in the process include ethylene, propylene, 1-butene, 3-methyl-1-butene, 4- methyl-1-pentene, 1-hexene, and 1-octene. It is particularly preferred to use supported or unsupported catalysts of this invention in the polymerization of ethylene, or propylene, or ethylene and at least one $C_3$–$C_8$ 1-olefin copolymerizable with ethylene. Typical diolefin monomers which can be used to form terpolymers with ethylene and propylene include butadiene, hexadiene, norbornadiene, and similar copolymerizable diene hydrocarbons. 1-Heptyne and 1-octyne are illustrative of suitable acetylenic monomers which can be used. Often the monomer or monomers being polymerized comprise(s) a 1-olefin, a vinylaromatic monomer, or an ester of acrylic or methacrylic acid.

The catalytic complexes of this invention can also be used for producing homopolymers and copolymers of certain functionally-substituted monomers or mixtures of monomers in which at least one monomer is a functionally-substituted monomer. One such group of functionally-substituted monomers which can be homopolymerized or copolymerized pursuant to this invention is comprised of monomers of the formula:

$$(R^5)(R^6)C=C(R^7)—COOR^8$$

wherein $R^5$, $R^6$, and $R^7$, are, independently hydrogen atoms or hydrocarbyl groups typically having up to about 20 carbon atoms, such as alkyl or aryl groups, and $R^8$ is a hydrocarbyl group such as an alkyl or aryl group having up to about 20 carbon atoms. When $R^5$, $R^6$, and/or $R^7$ are hydrocarbyl groups, each one present preferably is an alkyl group containing from 1 to 4 carbon atoms. Most preferably $R^5$ is a methyl group, $R^6$ is a hydrogen atom or methyl group, and $R^7$ is a hydrogen atom.

Polymerization of ethylene or copolymerization with ethylene and an α-olefin having 3 to 10 carbon atoms may be performed in either the gas or liquid phase (e.g. in a solvent, such as toluene, or heptane). The polymerization can be conducted at conventional temperatures (e.g., 0° to 120° C.) and pressures (e.g., ambient to 50 kg/cm²) using conventional procedures as to molecular weight regulations and the like.

The heterogeneous catalysts of this invention can be used in polymerizations conducted as slurry processes or as gas phase processes. By "slurry" is meant that the particulate catalyst is used as a slurry or dispersion in a suitable liquid reaction medium which may be composed of one or more ancillary solvents (e.g., liquid aromatic hydrocarbons, etc.) or an excess amount of liquid monomer to be polymerized in bulk. Generally speaking, these polymerizations are conducted at one or more temperatures in the range of about 0 to about 160° C., and under atmospheric, subatmospheric, or superatmospheric conditions. Conventional polymerization adjuvants, such as hydrogen, may be employed if desired. Preferably polymerizations conducted in a liquid reaction medium containing a slurry or dispersion of a catalyst of this invention are conducted at temperatures in the range of about 40 to about 110° C. Typical liquid diluents for such processes include hexane, toluene, and like materials. Typically, when conducting gas phase polymerizations, superatmospheric pressures are used, and the reactions are conducted at temperatures in the range of about 50 to about 160° C. These gas phase polymerizations can be performed in a stirred or fluidized bed of catalyst in a pressure vessel adapted to permit the separation of product particles from unreacted gases. Thermostated ethylene, comonomer, hydrogen and an inert diluent gas such as nitrogen can be introduced or recirculated to maintain the particles at the desired polymerization reaction temperature. An aluminum alkyl such as triethylaluminum may be added as a scavenger of water, oxygen and other impurities. In such cases the aluminum alkyl is preferably employed as a solution in a suitable dry liquid hydrocarbon solvent such as toluene or xylene. Concentrations of such solutions in the range of about $5 \times 10^{-5}$ molar are conveniently used. But solutions of greater or lesser concentrations can be used, if desired. Polymer product can be withdrawn continuously or semi-continuously at a rate that maintains a constant product inventory in the reactor.

Because of the high activity and productivity achievable by use of catalysts of this invention, the catalyst levels used in olefin polymerizations can be less than previously used in typical olefin polymerizations conducted on an equivalent scale. In general, the polymerizations and copolymerizations conducted pursuant to this invention are carried out using a catalytically effective amount of a novel catalyst composition of this invention, which amount may be varied depending upon such factors such as the type of polymerization being conducted, the polymerization conditions being used, and the type of reaction equipment in which the polymerization is being conducted. In many cases, the amount of the catalyst of this invention used will be such as to provide in the range of about 0.000001 to about 0.01 percent by weight of d- or f-block metal based on the weight of the monomer(s) being polymerized.

After polymerization and deactivation of the catalyst in a conventional manner, the product polymer can be recovered from the polymerization reactor by any suitable means. When conducting the process with a slurry or dispersion of the catalyst in a liquid medium the product typically is recovered by a physical separation technique (e.g. decantation, etc.). The recovered polymer is usually washed with one or more suitably volatile solvents to remove residual polymerization solvent or other impurities, and then dried, typically under reduced pressure with or without addition of heat. When conducting the process as a gas phase polymerization, the product after removal from the gas phase reactor is typically freed of residual monomer by means of a nitrogen purge, and often can be used without further catalyst deactivation or catalyst removal.

When preparing polymers pursuant to this invention conditions may be used for preparing unimodal or multimodal polymer types. For example, mixtures of catalysts of this invention formed from two or more different metallocenes having different propagation and termination rate constants for ethylene polymerizations can be used in preparing polymers having broad molecular weight distributions of the multimodal type.

The following Examples of polymerizations conducted pursuant to this invention are presented for purposes of illustration and not limitation.

EXAMPLE 18

Ethylene Polymerization

Ethylene polymerizations were carried out at room temperature in 250-mL flamed, round-bottom flasks attached to a high-vacuum line. In a typical experiment, a solution of each of the catalysts of Example 5 in 2 mL of toluene was quickly injected using a gas-tight syringe equipped with a spraying needle into respective rapidly-stirred flasks containing 100 mL of toluene which was pre-saturated under 1 atm of rigorously purified ethylene. The polymerization mixture was quenched with acidic MeOH at which point polyethylene precipitated. The respective polymers were collected by filtration, washed with MeOH and dried under high vacuum to a constant weight. Additional polymerizations were conducted using ethylene, ethylene and 1-hexene, styrene, and ethylene and styrene, using various catalyst systems. Conditions and results of these polymerizations are summarized in Tables 1–3.

TABLE 1

Comparison of Ethylene Polymerization Activities Mediated by Monomeric and Dinuclear Metallocene Cations Having Counteranions $MeB(C_6F_5)_3^\ominus$, $MePBB^\ominus$, and Polymer Properties[a]

| Entry | Catalyst | $\mu$mol of cat. | Reaction time (s) | Polymer yield (g) | Activity[b] | $10^{-3}M_w$ | $M_w/M_n$ |
|---|---|---|---|---|---|---|---|
| 1 | $Cp'_2ZrMe^\oplus MeB(C_6F_5)_3^\ominus$ | 0.15 | 60 | 1.0 | $4.0 \times 10^6$ | 124 | 2.03 |
| 2 | $[(Cp'_2ZrMe)_2(\mu\text{-Me})]^\oplus[MePBB]^\ominus$ | 0.15 | 40 | 0.8 | $4.8 \times 10^6$ | 559 | 3.06 |
| 3 | $Cp''_2ZrMe^\oplus MeB(C_6F_5)_3^\ominus$ | 0.15 | 60 | 1.5 | $6.0 \times 10^6$ | 321 | 1.42 |
| 4 | $[(Cp''_2ZrMe)_2(\mu\text{-Me})]^\oplus[MePBB]^\ominus$ | 0.15 | 40 | 1.3 | $7.8 \times 10^6$ | 392 | 2.72 |
| 5 | $Cp^*_2ZrMe^\oplus MeB(C_6F_5)_3^\ominus$ | 0.15 | 60 | 0.8 | $3.2 \times 10^6$ | 136 | 2.54 |
| 6 | $[(Cp^*_2ZrMe)_2(\mu\text{-Me})]^\oplus[MePBB]^\ominus$ | 0.15 | 60 | 1.1 | $4.4 \times 10^6$ | 370 | 2.28 |

[a]Carried our at 25° C., 1.0 atm of ethylene, and 100 mL of toluene on a high vacuum line.
[b]In units of grams of polymer/(mole of cat·atm·h).

TABLE 2

Summary of Ethylene (E) Polymerization, Ethylene-1-Hexene (E/H), and Ethylene-Styrene (E/S) Copolymerizations Catalyzed by Constrained Geometry Catalysts[a]

| Entry | Catalyst | Monomer | $\mu$mol of cat. | Reaction time (min) | Polymer yield (g) | Activity[b] | % Comonomer incorporation | $10^{-3}M_w$ | $M_w/M_n$ |
|---|---|---|---|---|---|---|---|---|---|
| 1 | $CGCZrMe^\oplus MeB(C_6F_5)_3^\ominus$ | E | 15 | 20 | 0 | 0 | | | |
| 2 | $[CGCZrMe]^\oplus[MePBB]^\ominus$ | E | 15 | 4 | 1.60 | $1.60 \times 10^6$ | | 7.69 | 2.78 |
| 3 | $CGCTiMe^\oplus MeB(C_6F_5)_3^\ominus$ | E | 15 | 10 | 0.20 | $8.00 \times 10^4$ | | 1058 | 9.54 |
| 4 | $[(CGCTiMe)_2Me]^\oplus[MePBB]^\ominus$ | E | 15 | 4 | 0.80 | $5.60 \times 10^6$ | | 305 | 2.56 |
| 5 | $CGCZrMe^\oplus MeB(C_6F_5)_3^\ominus$ | E/H | 50 | 15 | 0 | 0 | | | |
| 6 | $[CGCZrMe]^\oplus[MePBB]^\ominus$ | E/H | 50 | 15 | 6.97 | $5.58 \times 10^5$ | 33.6 | 10.0 | 2.68 |
| 7 | $CGCTiMe^\oplus MeB(C_6F_5)_3^\ominus$ | E/H | 25 | 10 | 0.05 | $1.20 \times 10^4$ | 63.2 | | |
| 8 | $[(CGCTiMe)_2Me]^\oplus[MePBB]^\ominus$ | E/H | 25 | 10 | 1.95 | $4.68 \times 10^5$ | 65.3 | 105 | 1.86 |
| 9 | $CGCTiMe^\oplus MeB(C_6F_5)_3^\ominus$ | E/S | 25 | 15 | 0.45 | $7.20 \times 10^4$ | 35.2 | | |
| 10 | $[(CGCTiMe)_2Me]^\oplus[MePBB]^\ominus$ | E/S | 25 | 15 | 0.80 | $1.28 \times 10^5$ | 33.4 | | |

[a]Ethylene (E) polymerizations were carried out at 25° C., 1 atm ethylene, and 100 mL of toluene on a high-vacuum line; ethylene-1-hexene (E/H) and ethylene-styrene (E/S) copolymerizations were carried out at 25° C., 0.356 M of ethylene, 1.78 of 1-hexene and styrene, and 25 mL of toluene on a high-vacuum line.
[b]In units of grams of polymer/(mole of cat·atm·h).

TABLE 3

Summary of Styrene Polymerization, and Ethylene-1-Hexene (E/H) Copolymerizations Catalyzed by Mono-Cp Metallocene Catalysts[a]

| Entry | Catalyst | Monomer | Reaction time (min) | Polymer yield (g) | Activity | $10^{-3}M_w$ | $M_w/M_n$ | Remarks |
|---|---|---|---|---|---|---|---|---|
| 1 | $Cp^*TiMe_3$-PBB | Styrene | 15 | 0.40 | $1.80 \times 10^6$ | 170 | 2.56 | [rrrr] = 98% |
| 2 | $[Cp^*ZrMe_2]^\oplus[MePBB]^\ominus$ | Styrene | 10 | 1.51 | $1.01 \times 10^7$ | | | atactic |
| 3 | $[Cp^*HfMe_2]^\oplus[MePBB]^\ominus$ | Styrene | 15 | 1.21 | $5.51 \times 10^6$ | 22.9 | 2.78 | atactic |
| 4 | $Cp^*HfMe_3$-$B(C_6F_5)_3$ | Styrene | 15 | 0.70 | $3.20 \times 10^6$ | 24.8 | 2.98 | atactic |
| 5 | $Cp^*TiMe_3$-$B(C_6F_5)_3$ | E/H | 5.0 | 0.70 | $1.70 \times 10^5$ | 848 | 23.7 | % H = 39.5 |
| 6 | $Cp^*TiMe_3$-PBB | E/H | 5.0 | 4.51 | $1.08 \times 10^6$ | 151 | 4.32 | % H = 43.6 |

[a]Styrene polymerizations (entries 1–4) were carried out at 25° C., 2.0 mL (17.4 mmol) of styrene, 50 $\mu$mol of catalyst, and 5 mL of toluene on high-vacuum line. Titanium catalysts were generated by in situ reaction of $CpTiMe_3$ + borane in 2 mL toluene. Activities in units of gram of bulk polymer/(mole of cat.)·(mole of monomer)·h; ethylene-1-hexene (E/H) copolymerizations (entries 5 and 6) were carried out at 25° C., 0.356 M of ethylene, 1.78 M of 1-hexene, 50 $\mu$mol of catalyst, and 25 mL of toluene on a high-vacuum line.

EXAMPLE 19

Propylene Polymerization

These reactions were carried out in a 100 mL quartz Worden vessel equipped with a magnetic stirring bar, a pressure gauge and a stainless steel O-ring assembly attached to a high vacuum line. In a typical experiment, the reaction vessel is flamed and then pumped under high vacuum for several hours, filled with inert gas and brought into a glove box. A measured amount of catalyst is added into the vessel. On the high vacuum line, a measured amount of the solvent and propylene are condensed at −78° C. The reaction apparatus is sealed off and warmed to the desired temperature. During the polymerization process, the reaction tube is immersed in a large amount of tap water (20–25° C.) or ice water (0° C.) to help dissipate the heat produced from the polymerization and keep the temperature constant. The progress of the polymerization reactions is monitored through observance of the pressure change. After the reaction is finished (pressure drops to zero psi), the resultant product is removed from the vessel, washed with methanol and water and dried under vacuum. Conditions and results of such polymerizations are summarized in Table 4.

TABLE 4

Isospecific and Syndiospecific Propylene Polymerizations Catalyzed by $C_2$- and $C_S$- Symmetric Metallocene/$B(C_6F_5)_3$, PBB, and $Ph_3C^{\oplus}B(C_6F_5)_4^{\ominus}$ Catalysts[a]

| Entry | Catalyst Reactants | μmol of cat. | $T_p$ (° C.) | Reaction time (min) | Polymer yield (g) | Activity[b] | $M_w \times 10^3$ | $M_w/M_n$ | $T_m$(° C.) | mmmm % |
|---|---|---|---|---|---|---|---|---|---|---|
| 1 | $Me_2Si(Ind)_2ZrMe_2$, $B(C_6F_5)_3$ | 10 | 24 | 2.5 | 0.73 | $1.8 \times 10^6$ | 32.6 | 2.40 | 146 | 93 |
| 2 | $Me_2Si(Ind)_2ZrMe_2$, $Ph_3C^{\oplus}B(C_6F_5)_4^{\ominus}$ | 2.0 | 24 | 4.0 | 0.77 | $5.8 \times 10^6$ | 123 | 1.94 | 147 | 93 |
| 3 | $Me_2Si(Ind)_2ZrMe_2$, PBB | 2.0 | 24 | 2.0 | 0.62 | $9.3 \times 10^6$ | 99.2 | 1.91 | 146 | 93 |
| 4 | $Me_2Si(Ind)_2ZrMe_2$, $B(C_6F_5)_3$ | 10 | 60 | 1.75 | 0.63 | $2.2 \times 10^6$ | 2.7 | 1.39 | 122 | 86 |
| 5 | $Me_2Si(Ind)_2ZrMe_2$, $Ph_3C^{\oplus}B(C_6F_5)_4^{\ominus}$ | 2.0 | 60 | 1.5 | 0.93 | $19 \times 10^6$ | 41.1 | 2.23 | 127 | 84 |
| 6 | $Me_2Si(Ind)_2ZrMe_2$, PBB | 2.0 | 60 | 1.0 | 0.53 | $16 \times 10^6$ | 43.6 | 2.04 | 130 | 86 |
| 7 | $Me_2C(Cp')(Flu)ZrMe_2$, $B(C_6F_5)_3$ | 20 | 24 | 40 | 3.15 | $2.4 \times 10^5$ | | | | 77[c] |
| 8 | $Me_2C(Cp')(Flu)ZrMe_2$, PBB | 20 | 24 | 20 | 3.53 | $5.3 \times 10^5$ | | | | 81[c] |

[a]All polymerizations carried out on high-vacuum line in 50 mL of toluene under 1 atm of propylene pressure.
[b]Gram of polymer/[(mole of cationic metallocene)·atm·h].
[c]% rrrr

EXAMPLE 20

Methyl Methacrylate Polymerization

A group of experiments were carried out to study the effectiveness of isolable, well-characterized cationic dinuclear complexes derived from PBB as compared to a catalyst system produced from $Cp_2ZrMe_2$ and tris (perfluorophenyl)borane. The conditions used and results obtained are summarized in Table 5.

TABLE 5

Methyl Methacrylate Polymerization Mediated by Dinuclear Cationic Complexes Derived From PBB[1]

| | | $T_p$ | Time | Conversion | Tacticity | | |
|---|---|---|---|---|---|---|---|
| Entry | Catalyst[b] | (° C.) | (h) | (%) | [mm] | [mr] | [rr] |
| 1 | $Cp'_2ZrMe^{\oplus}MeB(C_6F_5)_3^{\ominus}$ | 0 | 6.0 | 0 | | | |
| 2 | $[(Cp'_2ZrMe)_2(\mu\text{-}Me)]^{\oplus}[MePBB]^{\ominus}$ | 0 | 6.0 | 100 | 3.3 | 34.3 | 62.4 |
| 3 | $[(Cp'_2ZrMe)_2(\mu\text{-}Me)]^{\oplus}[MePBB]^{\ominus}$ | 25 | 2.5 | 100 | 3.8 | 36.0 | 60.2 |
| 4 | $[(Cp''_2ZrMe)_2(\mu\text{-}Me)]^{\oplus}[MePBB]^{\ominus}$ | 25 | 2.3 | 100 | 2.9 | 29.8 | 67.3 |
| 5 | $[(Cp*_2ThMe)_2(\mu\text{-}Me)]^{\oplus}[MePBB]^{\ominus}$ | 25 | 8.5 | 46 | 2.4 | 30.0 | 67.6 |
| 6 | $\{[rac\text{-}Me_2Si(Ind)_2ZrMe]_2(\mu\text{-}Me)\}^{\oplus}[MePBB]^{\ominus}$ | 0 | 5.5 | 100 | 93.0 | 4.8 | 2.2 |
| 7 | $[(CGCTiMe)_2(\mu\text{-}Me)]^{\oplus}[MePBB]^{\ominus}$ | 0 | 7.0 | 0 | | | |
| 8 | $[(CGCZrMe)_2(\mu\text{-}Me)]^{\oplus}[MePBB]^{\ominus}$ | 25 | 3.0 | 0 | | | |
| 9 | $\{[Me_2C(Cp')(Flu)ZrMe]_2(\mu\text{-}Me)\}^{\oplus}[MePBB]^{\ominus}$ | 0 | 6.0 | 0 | | | |
| 10 | $\{[Me_2C(Cp')(Flu)ZrMe]_2(\mu\text{-}Me)\}^{\oplus}[MePBB]^{\ominus}$ | 25 | 6.0 | 0 | | | |

[1]Conditions: 20 μmol catalyst; 2.0 mL MMA (18.7 mmol); MMA/cat., mol/mol = 935; 20 mL toluene; solvent/[$M_0$] = 10 vol/vol.
[b]Catalysts (entries 5 and 8) generated by in situ reaction of $2Cp_2MMe_2$ + PBB in 2 mL of toluene for 0.5 h.

EXAMPLE 21

Ethylene and Propylene Polymerizations

In order to compare the effectiveness of catalysts of this invention formed from bis(pentafluorophenyl)(2-perfluorobiphenyl)borane (BPB) with effectiveness of other catalytic species, several polymerizations were carried out using either ethylene or propylene. As above, on a high vacuum line ($10^{-5}$ torr), these polymerizations were carried out in a 250-mL round-bottom three-neck flask equipped with a large magnetic stirring bar and a thermocouple probe. A measured quantity of dry toluene was vacuum-transferred into the flask, saturated under 1 atmosphere of rigorously purified ethylene or propylene (pressured controlled using a mercury bubbler) and equilibrated at the desired reaction temperature using an external bath. The catalytic active species was freshly generated (within 1 minute) using a solution having a 1:1 metallocene:cocatalyst ratio in 1.5 mL of toluene. The solution of catalyst was then quickly injected into the rapidly stirred flask using a gas-tight syringe equipped with a spraying needle. The temperature of the toluene solution in representative polymerization experiments was monitored using a thermocouple (OMEGA Type K thermocouple with a Model HH21 microprocessor thermometer). The reaction exotherm temperature rise was invariably less than 5° C. during these polymerizations. After a measured time interval (short to minimize mass transport and exotherm effects), the polymerization mixture was quenched by the addition of 15 mL of 2% acidified methanol. Another 30 mL of methanol was then added and the polymer was collected by filtration, washed with methanol, and dried on the high-vacuum line overnight to a constant weight. Results of these polymerization experiments are summarized in Table 6. Uncertainties in activities reported in Table 6 are the average of 3 trials.

EXAMPLE 22

Polymerization of Tetrahydrofuran

A small amount of $\{[(C_5H_3Me_2)_2ZrMe](\mu\text{-Me})[MeZr(C_5H_3Me_2)]\}^{\oplus}[MePBB]^{\ominus}$ was loaded into a J-Young NMR tube and THF-$d_8$ was then vacuum-transferred into the tube. The mixture was slowly warmed to room temperature and left for several hours. The solid polymer formed in the tube was shown to be poly(tetrahydrofuran) by $^1$H analysis.

TABLE 6

Olefin Polymerization Data for Metallocenes Activated by [($C_6F_5$)$_2$B($C_{12}F_9$)] (BPB)[a]

| Entry | Catalyst | Monomer[b] | Temp (° C.) | Cat. μmol | Cond.[c] mL, min | Polymer yield (g) | Activity[d] × $10^5$ | $M_w^e$ × $10^3$ | $M_w/M_n$ | Remarks |
|---|---|---|---|---|---|---|---|---|---|---|
| 1 | [Cp'$_2$ZrMe]$^{\oplus}$[MeBPB]$^{\ominus}$ | ethylene | 23 | 15 | 100, 1.0 | 0.92 | 34(6) | 149 | 1.88 | |
| 2[f] | Cp'$_2$ZrMe$^{\oplus}$MeB(C$_6$F$_5$)$_3$$^{\ominus}$ | ethylene | 25 | 15 | 100, 1.0 | 1.00 | 40.0 | 124 | 2.03 | |
| 3 | [CGCTiMe]$^{\oplus}$[MeBPB]$^{\ominus}$ | ethylene | 23 | 15 | 100, 10 | 0.72 | 2.4(3) | 1330 | 7.90 | |
| 4[g] | CGCTiMe$^{\oplus}$MeB(C$_6$F$_5$)$_3$$^{\ominus}$ | ethylene | 25 | 15 | 100, 10 | 0.21 | 0.84 | 1058 | 9.54 | |
| 5 | [rac-Me$_2$Si(Ind)$_2$ZrMe]$^{\oplus}$-[MeBPB]$^{\ominus}$ | propylene | 24 | 10 | 50, 2.0 | 0.68 | 20(2) | 41 | 2.03 | $T_m$ = 146° C.; % mmmm = 93 |
| 6[h] | rac-Me$_2$Si(Ind)$_2$ZrMe$^{\oplus}$-MeB(C$_6$F$_5$)$_3$$^{\ominus}$ | propylene | 24 | 10 | 50, 2.5 | 0.73 | 18 | 33 | 2.40 | $T_m$ = 146° C.; % mmmm = 93 |

[a]All polymerizations carried out on a high vacuum line ($10^{-5}$ torr); uncertainties in activities are the average of 3 runs.
[b]Ethylene (E) and propylene (P) atm pressure.
[c]Conditions given as milliliters of toluene, time in minutes.
[d]Gram of polymer/[(mole of cationic metallocene)·atm·h].
[e]GPC relative to polystyrene standards.
[f]Data from Table 1 (reproducibility between runs ≈ 10–15%).
[g]Data from Table 2 (reproducibility between runs ≈ 10–15%).
[h]Data from Table 4 (reproducibility between runs ≈ 10–15%).

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A complex which comprises a cation formed from a d-block or f-block metal compound by loss of a leaving group and an anion formed by transfer of the leaving group to an organoborane of the formula:

$$BR'_nR''_{3-n}$$

wherein R' is a fluoroaryl group having at least one additional substituent other than fluorine, wherein each R" is, independently, (i) a fluoroaryl group having at least one additional substituent other than fluorine, or (ii) a fluorinated aryl group devoid of additional substitution, and n is 1 or 2.

2. A complex of claim 1 wherein the metal of said metal compound is a metal from Groups 4 to 8 of the Periodic Table.

3. A complex of claim 1 wherein the metal of said metal compound is thorium, titanium, zirconium, or hafnium.

4. A complex of claim 1 wherein said metal compound is a metallocene represented by the formula:

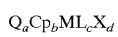

$$Q_aCp_bML_cX_d$$

where Cp independently in each occurrence is a cyclopentadienyl-moiety-containing group which has in the range of 5 to about 24 carbon atoms; Q is a bridging group or ansa group that links two Cp groups together; M is a d- or f-block metal atom; each L is, independently, a leaving group that is bonded to the d-or f-block metal atom and is capable of being abstracted by the triorganoborane used in forming the catalytic complex; X is a group other than a leaving group that is bonded to the d- or f-block metal atom and that does not detrimentally affect propagation of a polymer chain during polymerization; a is 0 or 1; b is a whole integer from 1 to 3; c is 1 to 3; d is 0 or 1; and the sum of c and d is at least 2.

5. A complex of claim 4 wherein M is a Group 4 metal atom, wherein a is 0, wherein b is 1, and the sum of c and d is 3.

6. A complex of claim 4 wherein M is a Group 4 metal atom, wherein b is 2 and the sum of c and d is 2.

7. A complex of claim 1 wherein said metal compound is a metallocene represented by the formula:

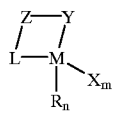

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group that does not detrimentally affect propagation of a polymer chain during polymerization, n is 1 to 4, m is 0 to 3, with the sum of n plus m being 1 to 4 depending upon the valence of M.

8. A complex of claim 7 wherein M is a titanium, zirconium or hafnium atom, L is a cyclopentadienyl group or a substituted cyclopentadienyl group, Z is a dihydrocarbylsilyl group, Y is a hydrocarbylamido group, R is methyl, n is 2, and m is 0.

9. A complex of claim 7 wherein M is a titanium or zirconium atom, L is a tetramethylcyclopentadienyl group, Z is a dimethylsilyl group, Y is a tert-butylamido group, R is methyl, n is 2, and m is 0.

10. A complex of claim 10 wherein said organoborane is a Lewis acid of a strength essentially equivalent to or greater than that of the corresponding organoborane in which each substituent other than fluorine is replaced by a fluorine atom.

11. A complex of claim 1 wherein said organoborane has a greater solubility in n-hexane at 20° C. than that of the corresponding organoborane in which each substituent other than fluorine is replaced by a fluorine atom.

12. A complex of claim 1 wherein said organoborane has the formula:

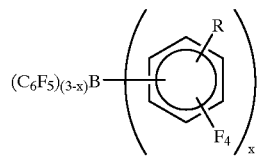

wherein R is a substituent other than a fluorine atom, and x is from 1 to 3.

13. A complex of claim 1 wherein said organoborane has the formula:

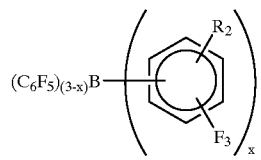

wherein each R is, independently, a substituent other than a fluorine atom, and x is from 1 to 3.

14. A complex of claim 1 wherein at least one said additional univalent substituent of said organoborane is an electron withdrawing substituent.

15. A complex of claim 1 wherein at least one said additional univalent substituent of said organoborane is a solubility-enhancing substituent.

16. A complex which comprises a cation formed from a d-block or f-block metal compound by loss of a leaving group and an anion formed by transfer of the leaving group to an organoborane of the formula:

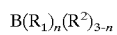

$$B(R_1)_n(R^2)_{3-n}$$

wherein each $R_1$ is, independently, a perfluorinated polycyclic fused ring group in which the ring system is totally aromatic or is partially aromatic and partially cycloaliphatic, wherein each $R^2$ is a pentafluorophenyl group, and wherein n is 1 to 3.

17. A complex of claim 16 wherein the metal of said metal compound is a metal from Groups 4 to 8 of the Periodic Table.

18. A complex of claim 16 wherein the metal of said metal compound is thorium, titanium, zirconium, or hafnium.

19. A complex of claim 16 wherein said metal compound is a metallocene represented by the formula:

where Cp independently in each occurrence is a cyclopentadienyl-moiety-containing group which has in the range of 5 to about 24 carbon atoms; Q is a bridging group or ansa group that links two Cp groups together; M is a d- or f-block metal atom; each L is, independently, a leaving group that is bonded to the d-or f-block metal atom and is capable of being abstracted by the triorganoborane used in forming the catalytic complex; X is a group other than a leaving group that is bonded to the d- or f-block metal atom and that does not detrimentally affect propagation of a polymer chain during polymerization; a is 0 or 1; b is a whole integer from 1 to 3; c is 1 to 3; d is 0 or 1; and the sum of c and d is at least 2.

20. A complex of claim 19 wherein M is a Group 4 metal atom, wherein a is 0, wherein b is 1, and the sum of c and d is 3.

21. A complex of claim 19 wherein M is a Group 4 metal atom, wherein b is 2 and the sum of c and d is 2.

22. A complex of claim 16 wherein said metal compound is a metallocene represented by the formula:

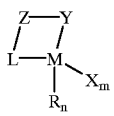

wherein M is a metal of Group 3 (other than scandium), Groups 4–10, or the lanthanide series; L is a group containing a cyclic, delocalized, anionic, pi-system through which the group is bound to M, and which group is also bound to Z; Z is a moiety comprising boron, or a member of Group 14 of the Periodic Table, and optionally sulfur or oxygen, this moiety having up to about 20 non-hydrogen atoms; Y is an anionic or nonanionic ligand group bonded to Z and M comprising nitrogen, phosphorus, oxygen, or sulfur, and having up to about 20 non-hydrogen atoms; R is a leaving group; X is a non-leaving group that does not detrimentally affect propagation of a polymer chain during polymerization, n is 1 to 4, m is 0 to 3, with the sum of n plus m being 1 to 4 depending upon the valence of M.

23. A complex of claim 22 wherein M is a titanium, zirconium or hafnium atom, L is a cyclopentadienyl group or a substituted cyclopentadienyl group, Z is a dihydrocarbylsilyl group, Y is a hydrocarbylamido group, R is methyl, n is 2, and m is 0.

24. A complex of claim 22 wherein M is a titanium or zirconium atom, L is a tetramethylcyclopentadienyl group, Z is a dimethylsilyl group, Y is a tert-butylamido group, R is methyl, n is 2, and m is 0.

25. A complex of claim 16 wherein said organoborane is tris(nonafluoroanthracenyl)borane, bis(nonafluoroanthracenyl)(pentafluorophenyl)borane, or (nonafluoroanthracenyl)bis(pentafluorophenyl)borane.

26. A complex of claim 16 wherein said organoborane is tris(undecafluorotetrahydronaphthyl)borane, bis(undecafluorotetrahydronaphthyl)(pentafluorophenyl) borane, or undecafluorotetrahydronaphthylbis(pentafluorophenyl)borane.

27. A complex of claim 16 wherein said organoborane is tris(nonafluorofluorenyl)borane, bis(nonafluorofluorenyl)(pentafluorophenyl)borane, or nonafluorofluorenylbis(pentafluorophenyl)borane.

* * * * *

UNITED STATES PATENT AND TRADEMARK OFFICE
CERTIFICATE OF CORRECTION

PATENT NO.    : 6,291,695 B1
DATED         : September 18, 2001
INVENTOR(S)   : Tobin J. Marks et al.

It is certified that error appears in the above-identified patent and that said Letters Patent is hereby corrected as shown below:

<u>Column 36,</u>
Line 10, claims dependency of "10" and should be -- 1 --.
Line 59, the formula reads "$B(R_1)_n(R^2)_{3-n}$" and should read -- $B(R^1)_n(R^2)_{3-n}$ --.
Line 60, reads "$R_1$" and should read -- $R^1$ --.

Signed and Sealed this

Thirtieth Day of April, 2002

*Attest:*

*Attesting Officer*

JAMES E. ROGAN
*Director of the United States Patent and Trademark Office*